US009213105B2

(12) United States Patent
Maeyama et al.

(10) Patent No.: US 9,213,105 B2
(45) Date of Patent: Dec. 15, 2015

(54) GEL DOSIMETER FOR MEASURING RADIATION DOSAGE AND MANUFACTURING METHOD THEREFOR

(71) Applicant: RIKEN, Saitama (JP)

(72) Inventors: Takuya Maeyama, Saitama (JP); Ryutaro Himeno, Saitama (JP); Shu Takagi, Saitama (JP); Nobuhisa Fukunishi, Saitama (JP); Shigeho Noda, Saitama (JP); Takuya Furuta, Saitama (JP); Kazuaki Fukasaku, Saitama (JP); Kenichi Ishikawa, Saitama (JP)

(73) Assignee: RIKEN, Saitama (JP)

( * ) Notice: Subject to any disclaimer, the term of this patent is extended or adjusted under 35 U.S.C. 154(b) by 13 days.

(21) Appl. No.: 14/226,104

(22) Filed: Mar. 26, 2014

(65) Prior Publication Data

US 2014/0295564 A1 Oct. 2, 2014

(30) Foreign Application Priority Data

Mar. 28, 2013 (JP) .................................. 2013-069797
Jan. 31, 2014 (JP) .................................. 2014-017201

(51) Int. Cl.
| G01T 1/04 | (2006.01) |
| G01T 1/02 | (2006.01) |
| G01T 1/00 | (2006.01) |
| G01N 33/60 | (2006.01) |
| G01N 33/80 | (2006.01) |
| G01N 33/58 | (2006.01) |
| G01N 33/50 | (2006.01) |

(52) U.S. Cl.
CPC . *G01T 1/04* (2013.01); *G01N 33/50* (2013.01); *G01N 33/60* (2013.01); *G01T 1/02* (2013.01)

(58) Field of Classification Search
CPC .............. G01T 1/04; G01T 1/02; G01T 1/00; G01N 33/60; G01N 33/80; G01N 33/58; G01N 33/50; G01N 33/48; G01N 33/00
USPC ...................................................... 436/58, 57
See application file for complete search history.

(56) References Cited

U.S. PATENT DOCUMENTS

2004/0211917 A1 10/2004 Adamovics

OTHER PUBLICATIONS

Bäck et al., "Ferrous sulphate gel dosimetry and MRI for proton beam dose measurements," *Phys. Med. Biol.* 44:1983-1996, 1999.
Maeyama et al., "Diffusion suppression in gel dosimetry by addition of nanoclay," *World Congress on Medical Physics and Biomedical Engineering, IFMBE Proceedings* 39:1183-1186, 2012.

*Primary Examiner* — Christine T Mui
(74) *Attorney, Agent, or Firm* — Seed IP Law Group PLLC

(57) ABSTRACT

To measure three-dimensional dose distributions with a dosimeter, such as a gel dosimeter. In an embodiment of the present invention, provided is a gel dosimeter having water, as solvent or disperse medium, clay particles that swell with water, and recording material precursor, which are dissolved or dispersed with each other. The recording material precursor has an atom or ion, wherein the atom or ion changes its valence number by reacting with both of a radical and a molecular radical derivative. The radical is to be generated from the water ionized by irradiation of radiation rays, and the molecular radical derivative is a molecule to be formed by bonding the radicals with each other. By the time radiation rays are irradiated, the gel dosimeter has been free from a substance identical to the molecular radical derivative and has lost fluidity.

19 Claims, 7 Drawing Sheets

GEL DOSIMETER FOR MEASURING RADIATION DOSAGE AND MANUFACTURING METHOD THEREFOR

CROSS-REFERENCE TO RELATED APPLICATIONS

This application is based upon and claims the benefit of priority to Japanese Patent Application No. 2013-069797, filed on Mar. 28, 2013 and Japanese Patent Application No. 2014-017201, filed on Jan. 31, 2014, the contents of all of which are incorporated herein by reference in their entirety.

BACKGROUND OF THE INVENTION

1. Technical Field

The present invention relates to a gel dosimeter for measuring radiation dose and manufacturing method therefor. More specifically, the present invention relates to a gel dosimeter for measuring radiation dose and manufacturing method therefor, for measuring three-dimensional dose distribution.

2. Background Art

Particle therapy using charged particle beams with high dose convergence, such as a proton beam, a heavy ion beam, including carbon and neon beams, has been introduced. The particle therapy is advantageous for its capability of controlling irradiation position and dose amount in the particle beam cancer treatment with higher accuracy than conventional X ray therapy. For the particle therapy, we should simultaneously pursue both of appropriate energy deposition from the particle beam to the target such as tumor position within the living body and suppression of damages to normal tissues surrounding the target position as much as possible. For this purpose, the spread of particle beam in diameter directions and the position of Bragg peak of the particle beam are adjusted to the target position in the irradiation object. Furthermore, a highly accurate therapy scheme called intensity modulated particle therapy (IMPT) is about to be practiced, in which accumulated doses of microscopic energy deposition at three-dimensional positions within the irradiation object, or dose distributions, are adjusted precisely. The amount of microscopic energy transfer due to ionization or excitation of molecules in a substance by a single particle is an energy deposit value per length transferred from the single particle to the substance, and is called a linear energy transfer (LET). The Bragg peak denotes a peak in the LET that is found near the endpoint of the range. Since the interaction with the substance, or the amount of ionization increases with inversely proportional to squared velocity of the incident particle, more amount of energy is deposited to the substance near the endpoint of the range by a particle such as positron or heavy ion. After accumulating the microscopic energy deposition at each point over particles, the dose amount at the point is obtained.

Dose distributions at three-dimensional points within the living tissue are optimized in treatment planning of the actual particle therapy. In typical treatment planning, a region where significant impact is exerted by the radiation is fit to an actual shape of the target tissue, on top of that the dose distribution in target tissue, i.e., point-by-point dose amount by the radiation, is also modified according to the therapy objective. At the same time, impact on surrounding healthy tissues is avoided, and impact especially on organ at risk is suppressed as much as possible. It should be noted that beams may be precisely controlled or irradiated multiple times to achieve intended treatment effect over a region with a complex shape extending in a width and a depth directions when using particle beams with high dose convergence that are usually adopted in the particle therapy. Schemes of the control may include shaping Bragg peak into the region as well as expanding a pencil beam and spreading the Bragg peak. For such purpose, particle irradiation device is equipped with auxiliary devices, like a wobbler and a ridge filter, and with filters and collimators, like a range shifter, a multi-leaf collimator, and a bolus, that will be adjusted to the irradiation object. For precise control in the radiation treatment, not only the whole device including the particle radiation device, the auxiliary devices, and the filter/collimator, but also irradiation process using such devices needs advanced quality assurance and quality control (hereinafter abbreviated to "QA/QC").

The QA/QC regarding the treatment planning and the devices requires technology that enables measurement of actual energy depositions caused by a large number of particles incident from various directions at various acceleration energies with proper accumulation capability. This is because the three-dimensional distribution of the energy depositions, or dose distribution, will be possible and thus the QA/QC will be supported, if an accurate measurement with accumulating the energies can be carried out at each position. Conventionally, such an object has been pursued with one- or two-dimensional dosimeters, such as ionization chamber dosimeters, semiconductor detectors, or film-type dosimeters. These types of dosimeters are used to obtain dose distributions along one- or two-dimensional coordinates for a region of particle beam that should be aligned at the target position. In addition to these, gel dosimeters have attracted much attention recently, in which a three-dimensional dose distribution can be measured by a gel material that operates under a measurement principle of chemical dosimeters. It is possible with the gel dosimeters to precisely measure energy values deposited by radiation at points within water, which could be regarded as a material equivalent to a living body. In other words, the gel dosimeters are advantageous for their measurement capability of radiation effect on a living body equivalent material or a water equivalent material. As a result, gel dosimeters can be used for measurement of three-dimensional dose distribution while using it as a solid phantom.

Types of gel dosimeters known to date are classified generally into: polymer gel dosimeters, Fricke gel dosimeters, and dichromic acid gel dosimeters (dichromate gel, or DCG dosimeters). Of these types, the polymer gel dosimeters that record cross-link reaction of pre-polymer have already solved a problem caused by diffusion (see, for example, Patent Document 1). On the other hand, the Fricke gel dosimeters, which have gel of aqueous solution of ammonium iron(II) and iron(II) sulfate, and the DCG dosimeters, which have gel of aqueous solution of chromium dioxide (chromium(IV) oxide) have problems that the images therein will become indistinct over time due to diffusion after the irradiation. Thus, the inventors of the present application have tried to suppress such diffusion by mixing clay particles called nanoclay into Fricke Xylenol gel (FXG) dosimeters, a type of Fricke gel dosimeters, and into DCG dosimeters as irradiation object, and have succeeded in sustaining the recordation over time to a certain level (Non Patent Document 1).

REFERENCES

Patent Document

Patent Document 1: U.S. Patent Application Publication No. 2004/0211917 A1

Non-Patent Documents

Non-Patent Document 1: T. Maeyama et al., "Diffusion suppression in gel dosimetry by addition of nanoclay", World Congress on Medical Physics and Biomedical Engineering May 26-31, 2012, Beijing, China, IFMBE Proceedings Volume 39, pp 1183-1186 (2013)

Non-Patent Document 2: Seven Back et al., "Ferrous sulphate gel dosimetry and MRI for proton beam dose measurements", Phys. Med. Biol., Volume 44 No. 8, pp 1983-96 (1999)

SUMMARY OF THE INVENTION

Technical Problem

In addition to the problems stated above, conventional gel dosimeters suffer from a problem with significant dose response dependence of their material on beam quality. The dose response in the gel dosimeters is a quantitative response relationship between the accumulated microscopic energy deposition over the particles and recording material density. More specifically, the recording material density is an amount or density of material that record the dose amount in the gel dosimeter, which is any material used for recording the dose amount. The problem is found in a dose response that is required for locally accumulating the microscopic energy deposition. The dose response may be explained concisely as a gradient coefficient, or slope, of the recording material density (response of the gel) when recording the increase of the dose amount while the microscopic energy deposition is accumulated. The response in the gel dosimeter after irradiation can be read out in a form of a distribution over three-dimensional positions by way of MRI or optical CT apparatus. One specific property in the radiation quality that is relevant to the dose response is a linear energy transfer (LET). The LET is an energy deposition per unit length at each position where an irradiated particle travels while transferring its own energy to the material until it stops at its endpoint of the range.

Let us assume a case when precise calculation of physical dose amount should be carried for performing a measurement with a gel dosimeter for the purpose of test irradiation when establishing therapy plan or a QA/QC purpose. For that purpose, the dose response shall not be affected by the radiation quality as much as possible, and the dose response to the microscopic energy deposition at each position shall be constant. This is because the physical dose to be determined at the target, such as a human body, the gel dosimeter etc., is considered to be an LET value of each particle at each position that is to be accumulated over all the particles. For example, for an irradiation condition in which a number of particles come from multiple incident directions, or for another irradiation condition in which the filter/collimator is placed in travel paths of the particles, and particles of different LETs with various energy values and various depths, i.e., different radiation qualities may deposit their energy at positions. If the recording material density fails to respond linearly to the actual microscopic energy deposition, it is impossible to measure actual macroscopic energy deposition at each position, or to measure dose response with accuracy by the gel dosimeters.

However, it is impossible to determine the macroscopic energy deposition at positions, or the dose distribution in principle with conventional gel dosimeters, because the dose response depends on the radiation quality and no linear relationship is established, thereby the accumulation remains improper. Without proper accumulation of the microscopic energy deposition in the recording material density, it is also impossible to recover through subsequent mathematical conversion. As stated above, the conventional gel dosimeters need further improvement when they are applied in establishing treatment plans for the therapy using the radiation irradiation apparatus and when they are applied to the QA/QC of such apparatus itself or to irradiation treatment with such apparatus.

Furthermore, gelling agent is used for gel formation in the conventional gel dosimeters, such as gelatin or agarose, for Fricke gel dosimeter and DCG dosimeter. Therefore, heating with stirring and subsequent cooling are necessary when preparing the gel dosimeters if the gelling agent is gelatin. The gelatin may be decomposed due to thermolysis if the temperature during the heating exceeds its optimum temperature. Preparation process accompanying such temperature change is difficult to carry out with high reproducibility, and therefore, it needs high skills for manufacturing high accuracy dosimeters. Such a difficulty may be caused by variation of saturation concentration of dissolved oxygen due to temperature variation, and by possible oxidation due to the heat.

The present invention is devised for solving at least any of such problems. That is, the present invention provides a gel dosimeter and a method for manufacturing the same for an accurate measurement of three-dimensional dose distribution of particle beams with respect to the particle irradiation apparatus and irradiation processes with such an apparatus. Moreover, the present invention provides a gel dosimeter and a method for manufacturing the same without using gelling agents, allowing not only easy preparation but also high sensitivity for the gel dosimeter and the manufacturing methods. As a result, the present invention realizes establishing the treatment plan and QA/QC in the particle irradiation apparatus and the radiation process with it, and contributes to improve practicability of the particle therapy.

Solution to Problem

The inventors of the present invention have sought for a specific solution to solve the problems mentioned above and have paid attention to mechanisms with which the microscopic and macroscopic energy depositions are measured in the conventional gel dosimeters, especially to how the recording material is formed. Moreover, the inventors estimated that it would be possible to alleviate or remove dose response dependence on radiation quality regarding the response of the recording material if we can use a reaction mechanism for the recording material formation, where the reaction mechanism has never been used for recording materials formation. The amount of response for the recording material means in this context recording materials density, in amounts per unit volume. The inventors of the present invention have confirmed experimentally that our estimation actually works and have conceived of specific structures of the gel dosimeters that adopt such reaction mechanisms.

Accordingly, in one aspect of the present invention, provided is a gel dosimeter for measuring radiation dose comprising: water, as solvent or disperse medium; clay particles; and recording material precursor having an atom or ion, wherein the atom or ion changes a valence number by reacting with both of a radical and a molecular radical derivative, the radical being any of radicals to be generated from the water ionized by irradiation of radiation rays, and the molecular radical derivative being a molecule to be formed from the radicals that are bonded with each other, wherein the water, the clay particles, and the recording material precursor are dissolved or dispersed with each other, wherein the gel dosimeter is free from a substance identical to the molecular radical derivative before radiation rays are irradiated, and wherein the gel dosimeter has lost fluidity by the time radiation rays are irradiated.

In addition, in another aspect of the present invention, provided is a method for manufacturing a gel dosimeter for measuring radiation dose comprising: a step of forming the gel dosimeter by dissolving or dispersing water, clay particles, and recording material precursor with each other, wherein the water is solvent or disperse medium, and the recording material precursor has an atom or ion, wherein the atom or ion changes a valence number by reacting with both of a radical and a molecular radical derivative, the radical being any of radicals to be generated from the water ionized by irradiation of radiation rays, and the molecular radical derivative being a molecule to be formed from the radicals that are bonded with each other, wherein the step of forming the gel dosimeter includes a step of eliminating fluidity of the gel dosimeter by the time radiation rays are irradiated, and wherein the method further comprising, at any stage before the gel dosimeter is formed, a step of removing the molecular radical derivative by excluding a substance identical to the molecular radical derivative from the gel dosimeter to be formed.

In the aspects of the present invention a gel dosimeter is a substance per se that has lost fluidity typically by being provided with gel consistency, while having three-dimensional volume and the dose amount recording capability by radiation in the material. However, it should be noted that, the gel dosimeter does not always need to form a gel in the strict sense, so long as it has lost the fluidity. If we name examples to indicate the state of having lost the fluidity from common articles, they will include curd materials like yogurt or cheese, bread dough, tomato ketchup, and jelly. That is, the expression "gel" for gel dosimeters in the aspects of the present invention is based on customary expression and is meant only to denote consistency of having lost the fluidity, while being a form of mixture like dispersion as a whole and being capable of recording the radiation dose amount. The gel consistency in this context is obtained as a result of the gelling agent or other ingredients. It should be noted that it is possible for the dosimeter to lose its fluidity even when no gelling agent is added, i.e., when no such substance as usually adopted for gelling purpose like gelatin or agarose is added but clay particles exist together with water. After detailed experiments, we have manufactured dosimeters that have lost the fluidity with at least shape retention nature (solidity) not only in the case when a gelling agent is added, but also when gelling agent is absent, which will be described later. Solidity for such dosimeters is confirmed to be originated by functions of other materials than gelling agent, for example, by solvent or dispersion including water and clay particles. For the clarity of the description, the "gelling agent" in the present application shall not include clay particles, even when the clay particles have a nature of such solidification.

Furthermore, the atom or ion that is contained in the recording material precursor may include one that becomes a part of the recording material precursor in a chemical form of ion or the like under the influence of water in the gel dosimeter.

The "molecular radical derivative (MRD)" in the aspects of the present invention shall denote any material that has been formed as a derivative through reaction between radicals among water-originating radicals that are generated by the radiation, but excluding the radicals themselves. The reaction in the above is hereinafter called "radical self-consuming reaction". The status of "free from a substance identical to the MRD" or the operation of "removing the MRD" is not limited to a state or an operation in which the substance identical to the MRD is totally absent nor a state in which such a substance is totally undetected. That is, the status or the operation should be considered to include a status substantially free from the substance or an operation substantially removing the substance. If we give examples for describing "substantially free from the substance but substance identical to the MRD may exist in the gel dosimeter", they will include a case when all the substance identical to the MRD is fixed, such as by being separated out in a manner they have no relationship with operation of measuring radiation by the gel dosimeter. Another example is a case when the substance identical to the MRD is reduced to an extent that the residual part would not cause any problem. These examples should apply also to "removing the MRD".

Advantageous Effect of the Invention

According to a gel dosimeter provided in the aspects of the present invention it is possible to accurately measure three-dimensional dose distribution of particle beams while reducing or removing dependence on radiation quality, especially on the LET, from dose response of a gel dosimeter. According to the aspects of the present invention, it will become possible to adopt a gel dosimeter for measuring three-dimensional dose distribution in establishing a treatment plan that uses particle radiation or in QA/QC of the radiation irradiation apparatus and related irradiation processes.

Furthermore, according to the aspects of the present invention, it is possible to measure three-dimensional dose distribution without containing gelling agents such as gelatin, agarose or the like, and the sensitivity is improved, thereby highly practical gel dosimeters can be provided.

DESCRIPTION OF THE EMBODIMENT

The embodiments (Embodiments 1 and 2) of the present invention will be described. For all drawings, the common reference signs are given to common parts or elements unless otherwise noted. For the description of the embodiments, conventional gel dosimeters in the first place; then in comparison with the conventional ones we specifically describe an embodiment (Embodiment 1) of the gel dosimeter having gelling agent. Thereafter, we describe an embodiment (Embodiment 2) that has no gelling agent in comparison with Embodiment 1.

1. Conventional Gel Dosimeters

In the first place conventional gel dosimeters and their characteristics are described for explaining our concept in the present invention.

1-1. Principle of Dose Measurement and Measurement Examples

Figure 1:
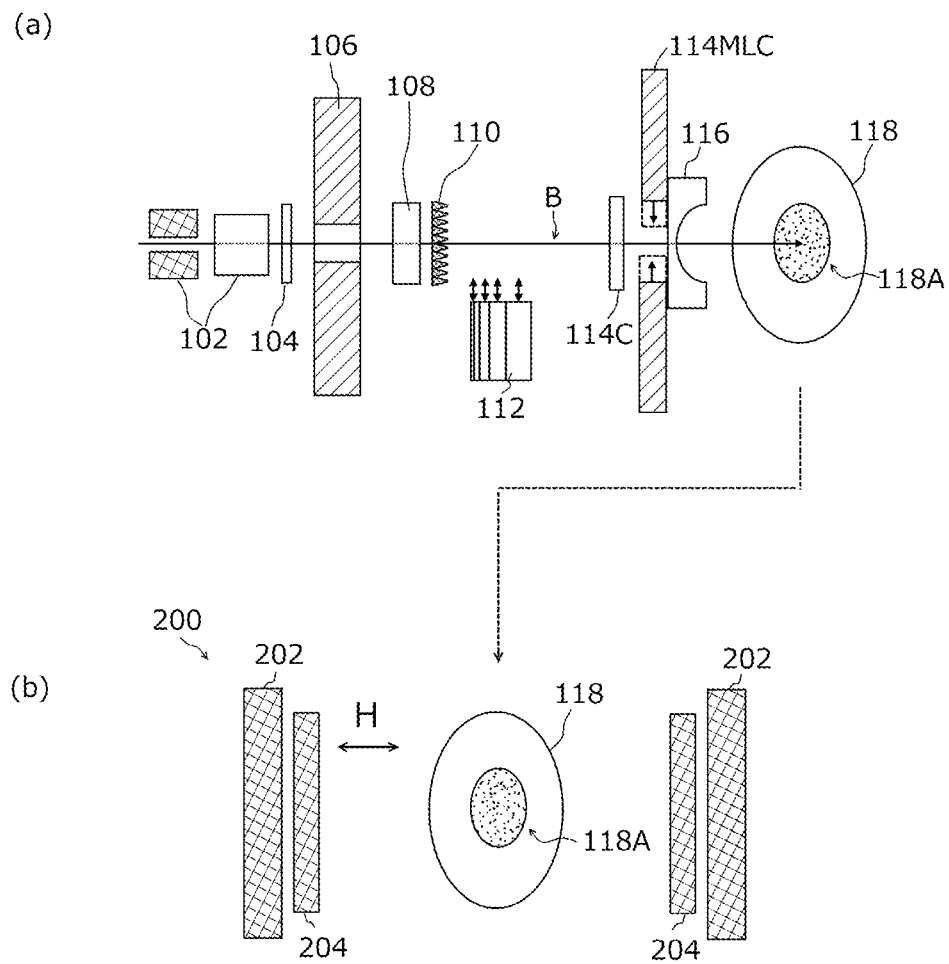
FIG. 1 is a schematic diagram illustrating irradiation of particle beam and the subsequent measurement for a conventional gel dosimeter and for dosimeters in Embodiments 1 and 2 of the present invention.
Figure 2:
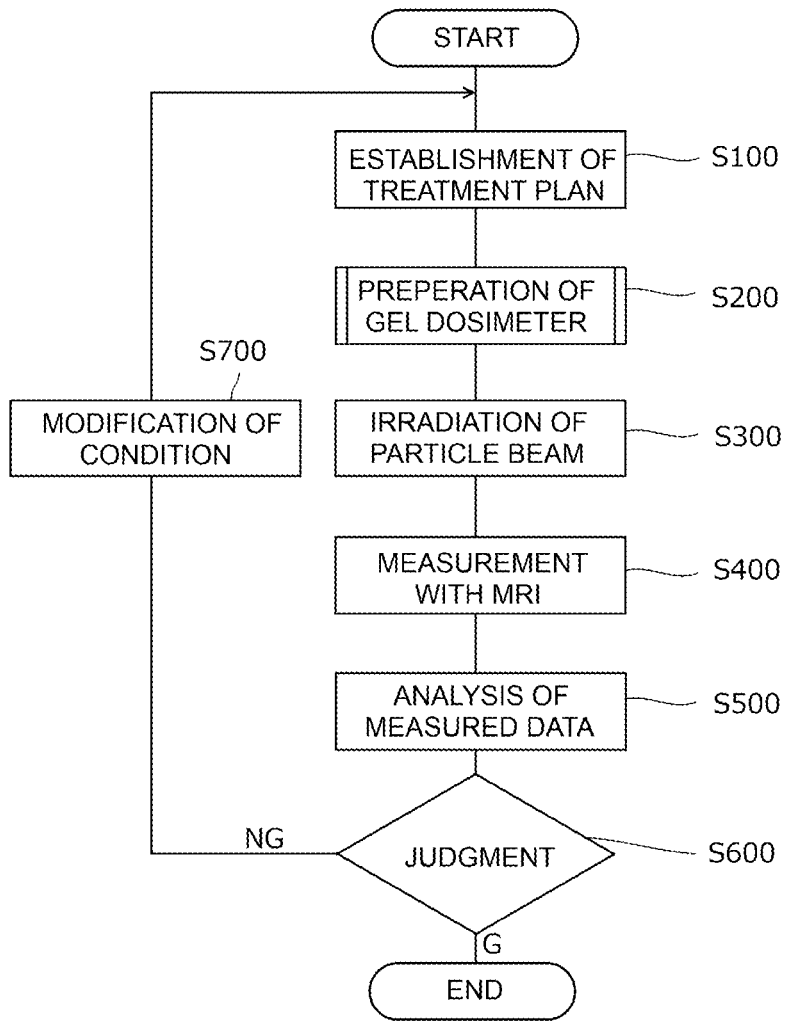
FIG. 2 is a flowchart indicating processes of irradiation of particle beam to gel dosimeters and subsequent measurements based on an example for establishing a treatment plan in Embodiments 1 and 2 of the present invention.

FIG. 1 is a schematic diagram illustrating irradiation of particle beam and the subsequent measurement for a conventional gel dosimeter and dosimeters in Embodiments 1 and 2. FIG. 2 is a flowchart indicating processes of irradiation of particle beam to gel dosimeters and subsequent measurements based on an example for establishing a treatment plan in Embodiments 1 and 2.

FIG. 1 depicts schematic diagrams that indicate irradiation arrangement for irradiating a particle beam to a gel dosimeter in FIG. 1a and measurement arrangement for measuring recording material density in the gel dosimeter after the irradiation in FIG. 1b. As indicated in FIG. 1a, a particle beam B is irradiated to a dosimeter 118, an irradiation object. The gel dosimeter 118 records a dose distribution inside of itself in the form of recording material density and, at the same time, behaves by itself as a phantom having water-equivalent materials in place of a real irradiation object, such as a human body. The dose distribution is schematically illustrated as a record density distribution 118A. Therefore, relative geometric arrangements of the particle beam B to be irradiated to the gel dosimeter 118 are controlled in various forms. The particle beam B is generated as a monochromatic beam with a single energy by an accelerator (not shown), and is expanded to have a predetermined cross-section region by way of a wobbler magnet 102, a scatterer 104, and a screen with aperture 106. There is provided a monitor sensor 108 to monitor the intensity of particle beam B. The particle beam B then passes through a ridge filter 110 and is expanded in directions perpendicular to the beam travel direction such that Bragg peaks have an extent encompassing the intended target region within the irradiation object. Then the beam B passes through a range shifter 112, which is provided to adjust ranges of the particle beam B. The range shifter 112 has a function to adjust the ranges from incident surface to fit them to the intended target region in the irradiation object, such as a human body and a gel dosimeter 118. Thereafter, for adjustment of the periphery of a cross-section of particle beam B, the outline periphery is trimmed by a collimator 114C, and the detailed periphery is defined by the multi-leaf collimator 114MLC according to the intended target region. The particle beam B passes through a compensator, or the bolus 116, whose three-dimensional surface contour has been tailored according to the target region within the irradiation object such that SOBP (spread out Bragg peak) of the particle beam B fits interior of the front and rear surfaces of the intended target region in depth direction. As a result, the particle beam B is carefully controlled and adjusted according to the irradiation object, and the dose distribution of the particle beam B is recorded as a record density distribution 118A of the gel dosimeter 118 that is equivalent to the living body.

As indicated in FIG. 1b, the record density distribution 118A in gel dosimeter 118 after irradiation is measured by an MRI apparatus 200. This measurement allows measurement of a physical dose distribution in a preferable case when the record density distribution 118A at positions in the gel dosimeter 118 records local accumulation value of microscopic energy deposition. Specifically, an alternating magnetic field H is applied to the gel dosimeter 118 by the MRI apparatus 200 with rotating excitation coils 202, and response signals from positions within the gel dosimeter 118 are received by pick-up coils 204. In this way, the density values of recording material at positions within the gel dosimeter 118 are measured. The density values of the recording material are recorded in a format of voxel data or the like, the density values at positions are subsequently read out, and they are made displayable as a tomography image at arbitrary positions. Such processes of irradiation and measurement are common regardless of whether the gel dosimeter 118 is of conventional gel dosimeter or of a gel dosimeter in Embodiment 1 or 2. Moreover, even for different types of gel dosimeters, the processes stated above are generally identical, except for measured values, or types of relaxation rates, detected by the MRI apparatus.

As indicated in FIG. 2, a dose distribution that gives necessary dose depositions at positions is assumed, and a medical professional establishes a treatment plan accordingly, with the help of computers as necessity (Step S100) in the particle therapy. More particularly, he/she determines irradiation conditions including arrangements, directions, dose amount (irradiation duration), and settings of filters and collimators. Meanwhile, the irradiation conditions are determined such that the dose amounts would give planned values at positions in the irradiation region, whereas unnecessary effect would be prevented at positions other than the irradiation region. At least one irradiation sequence is determined for the treatment plan. Next, a gel dosimeter is prepared (Step S200). Basically one gel dosimeter is manufactured for one irradiation sequence of the treatment plan for determination as to whether the treatment plan is appropriate or not. The processing order between the establishing of the treatment plan (Step S100) and the preparing of a gel dosimeter (Step S200) may be exchanged as necessity. The gel dosimeter as irradiation object is then irradiated with the particle beam according to the treatment plan (Step S300). The gel dosimeter after the irradiation is measured with respect to the recording materials density by an MRI, for example (Step S400). The measurement may be carried out by any other apparatus for detecting the recording material in the gel dosimeter than the MRI, such as x-ray CT apparatus, ultrasonic echo apparatus, or arbitrary nondestructive measurement apparatuses, and any measurement apparatus that requires destruction of the gel dosimeter as well. The measurement data is analyzed in an appropriate way (Step S500), and judgment is made on the analyzed result by a medical professional including a physician or a radiologic technologist (Step S600). If the result is judged as satisfactory, then the sequence of processes will go to the end (Branch G). In contrast, if the result is not judges as satisfactory (Branch NG), then the conditions are modified (Step S700) and the establishing step of the treatment plan will be retried (Step S100). The modification of the condition is mainly related to adjustment of a beam direction, adjustment of dose amount, replacement of filters, and adjustment of the settings for the filters, and so on. When the gel dosimeter is adopted when establishing actual treatment plans, other modifications that can be practiced easily by a person skilled in the art may be made by following the above-mentioned scheme in principle. For example, plural gel dosimeters are used for consecutive radiation processes based on plural irradiation sequences, and the plural gel dosimeters are compared for judgment. Moreover, instead of establishing treatment plans, performances of the particle irradiation apparatus and its auxiliary devices, including reproducibility in the dose amount, the spreading of beams, and so forth, are checked for QA/QC purposes using actually measured values of the dose distribution by the gel dosimeters, and the operation conditions for the apparatus and auxiliary devices are adjusted if necessary.

Possible conventional gel dosimeters that may be used for the above mentioned operation, assuming sufficient performances are achieved, include Fricke gel dosimeters, dichromate gel dosimeters (DCG dosimeters), polymer gel dosimeters and so forth.

The final objective for measuring the dose distribution is a simultaneous pursuit, in an appropriate manner, of the controlled energy deposition from the particle beam to the target positions such as tumor and the suppression of damages to surrounding normal tissues as much as possible, when irradiating the irradiation object such as a human body with the radiation. Specifically, after irradiation of the radiation, free radicals originated from water ionized by the radiation acts on the living tissue by damaging or breaking DNAs or the like. The strength of the action depends typically on dose amounts at positions in the irradiation object. It should be noted that dose distribution in the description of the present application means positional distribution. That is, the dose distribution denotes a distribution of effects caused by irradiation expressed in a spatial resolution that is applicable for the purpose of at least treatment planning and QA/QC, where the distribution of effects, such as macroscopic energy deposition is obtained at positions in the irradiation object. The macroscopic energy deposition for the physical dose amount is obtained by LETs, for each particle having a specific energy value, multiplied by fluence per the energy value, then integrating the foregoing over the entire energy values for the irradiated particle beam, and again integrating the foregoing result over the irradiation time duration.

Gel dosimeters operate such that the macroscopic energy depositions are recorded by density values of the recording material through chemical reaction relevant to water-originating radicals. The water-originating radicals are relevant to each of the gel dosimeters mentioned above through such phenomena as oxidization of Fe(II) ion (in Fricke gel dosimeters), reduction of $Cr_2O_7^{2-}$ (in DCG dosimeters), and polymerization from pre-polymers (in polymer gel dosimeters). The recording materials are Fe(III) ion (in Fricke gel dosimeters), $Cr^{3+}$ (in DCG dosimeters) and polymerized polymer (in polymer gel dosimeters).

When it comes to detailed mechanisms in the gel dosimeters, water, one of primary ingredients, is ionized or excited by ionization after acquiring energy by a particle beam such as carbon beam. The ions or excited water molecules are decomposed immediately, to generate relatively long lifetime water-originating radicals. As a result of reactions of binding such radicals with each other, or "radical self-consuming reaction", some types of water-originating radicals once generated as radicals are converted into different molecular products. We call substances that are derived from the radicals via the radical self-consuming reaction, excluding the radicals by themselves, as "molecular radical derivatives (MRDs)" in this application. Typical water-originating radicals are $e_{aq}^-$ (hydration electron), .H (hydrogen radical), and .OH (hydroxyl radical). In contrast, typical MRDs are $H_2O_2$ (hydrogen peroxide), $H_2$ (hydrogen), and $O_2$ (oxygen). In this regard, MRDs may include electron, radicals, and ions as well as atoms and molecules.

A required characteristic for ideal gel dosimeters that measure the physical dose amount is that the increment of recording material density at positions within the gel dosimeter reflects microscopic energy deposition at the positions while maintaining accumulation capability. The relationship that should be satisfied for that accumulation capability is, in short, as follows:

microscopic energy deposition ∝ increment of recording material density,            Formula (1), where, the symbol "∝" stands for proportionality of both sides therebetween. Considering the gel dosimeters' property that the microscopic energy deposition is accumulated and recorded, the microscopic energy deposition in Formula (1) shall be local energy deposition, and, not only that, it shall be energy deposition incrementally deposited through interactions by a sequence of incoming particles. In the following description, microscopic energy deposition in the gel dosimeters should satisfy these relationships, unless otherwise noted.

In the case of the conventional gel dosimeters, the recording material density increases according to density of water-originating radicals that forms the recording material, where the radical density is determined by ionization density at positions within the dosimeter, and where the ionization density at positions is determined by the microscopic energy deposition. Thus, to make certain the ideal operation in Formula (1) for the conventional gel dosimeters a chain of proportionalities should be established, as follows:

microscopic energy deposition ∝ ionization density ∝ radical density ∝ increment of recording material density,            Formula (2).

Meanwhile, studies to date have revealed quantitative efficiencies of production, G values, for relationships between energies given to living tissues or gel dosimeters through water by radiations, and average amounts of chemical species produced therefrom, or the number of radicals, molecules, or ions. The G values are expressed as average numbers of formation for each of chemical species per $1.602 \times 10^{-17}$ J (100 eV). For example, in an acid environment, the G values are:

$G(e_{aq}^- + .H) = 3.7$,
$G(.OH) = 2.9$,
$G(H_2) = 0.4$, and
$G(H_2O_2) = 0.8$.

These relationships exist for any gel dosimeters having water as one of their primary ingredients and for actual living tissues as well.

From now on, based on an example of Fricke dosimeter for the types of gel dosimeters, further description will be made regarding mechanisms, through which the dose amount is measured by the conventional gel dosimeters, and the measurement example therefor. A reaction mechanism initiated by irradiation of radiation rays to Fricke gel dosimeters is oxidation of Fe(III) ions ($Fe^{2+}$) to iron(III) ions ($Fe^{3+}$) in aqueous solutions of ammonium iron(II) and iron(II) sulfate. Thus a substance that may include or form iron(II) acts as the precursor for the recording material, and iron(III) ions acts as the recording material. The G value for the forming iron(III) ions from iron(II) ions is 15.6 ($1/100$ eV), and the G value for iron(III) ion satisfies a following relationship with G values for the radicals and the MRDs to be produced from water upon irradiation of radiations:

$$G(Fe(III))=G(.OH)+2(G(H_2O_2))+3(G(e_{aq}^-)+G(.H)+G(HO_2.)) \quad \text{Formula (3),}$$

where, $G(e_{aq}^-)+G(.H)+G(HO_2.)=G(e_{aq}^-+.H)$.

For determination of dose amounts at positions, three-dimensional measurement with arbitrary measurement means is carried out for production amount or record density of iron(II) ions, at positions within the Fricke gel dosimeter irradiated with radiations. As explained in connection with FIG. 1, dosimeters having transitional metals such as Fricke gel dosimeters and DCG dosimeters and dosimeters as polymer gel dosimeters can be usually measured for their recording material density by an NMR. The density of iron(III) ions, the recording material in the Fricke gel dosimeters, is proportional to longitudinal relaxation rates (spin-lattice relaxation rates) $R_1=1/T_1$, thus values for longitudinal relaxation times (spin-lattice relaxation times) $T_1$ are measured by the NMR. The densities of iron(I) ions as scalar values at positions in the gel dosimeters can be converted to voxel data or images in the final result. In the case of other gel dosimeters, values of $R_1=1/T_1$ are similarly measured for DCG dosimeter, in a similar fashion. For polymer gel dosimeters, lateral relaxation rates (spin-spin relaxation rates) $R_2=1/T_2$ are measured.

As explained above, what needs to be focused regarding the density of recording material in the gel dosimeters is either linearity of the dose response, or proportionality between the increment of density of the recording material in Formula (1) and the microscopic energy deposition. In this application, the existence of these proportionalities is shown in a form of a graph comparable with a graph obtained for curves of macroscopic energy depositions with Bragg peaks, which is a graph for actually measured dose distribution. This can be explained by way of example with the Fricke gel dosimeters, as follows: in the first place, a gradient $\delta R_1$ of the longitudinal relaxation time $R_1$ is determined while changing the dose amount. Then, instead of the values per se of the gradient $\delta R_1$ of $R_1$ against dose amounts at positions within the gel dosimeter, the gradient $\delta R_1$ is expressed in a graph of relative values of the gradient $\delta R_1$ of $R_1$ to a dose value at the surface of the gel dosimeter. The gradients $\delta R_1$ at positions will be proportional to the actual measurement values of the dose amount for the particle beam, such as a graph having a shape of increments due to LET actually measured by ionization chamber, if the gradients $\delta R_1$ at positions precisely reflect increments of the microscopic energy dose. This means that a graph of the gradients $\delta R_1$ in the above mentioned expression forms the same curve as the actual dose, except for scale differences. Furthermore, when indicating a graph of $\delta R_1$, we plot a graph of the gradients $\delta R_1$ with normalized values, or relative dose amount, with a value at the surface of the gel dosimeter for carrying out the comparison easily. As a result, the graphs for the gradients $\delta R_1$ and for the actually measured values of the macroscopic energy deposition have corresponding shapes with each other. In the case when the ideal performance is achieved, the graphs will perfectly match with each other even for the Bragg peaks for monochromatic particle beams. In contrast, in the case when the density of the recording material is not proportional to the microscopic energy deposition, the discrepancy between the gradients $\delta R_1$ and the actually measured values will be observed as a difference of their graphical shapes. This circumstance is the same when the polymer gel dosimeter is adopted and the gradients $\delta R_2$ are measured in a graph.

Figure 3:
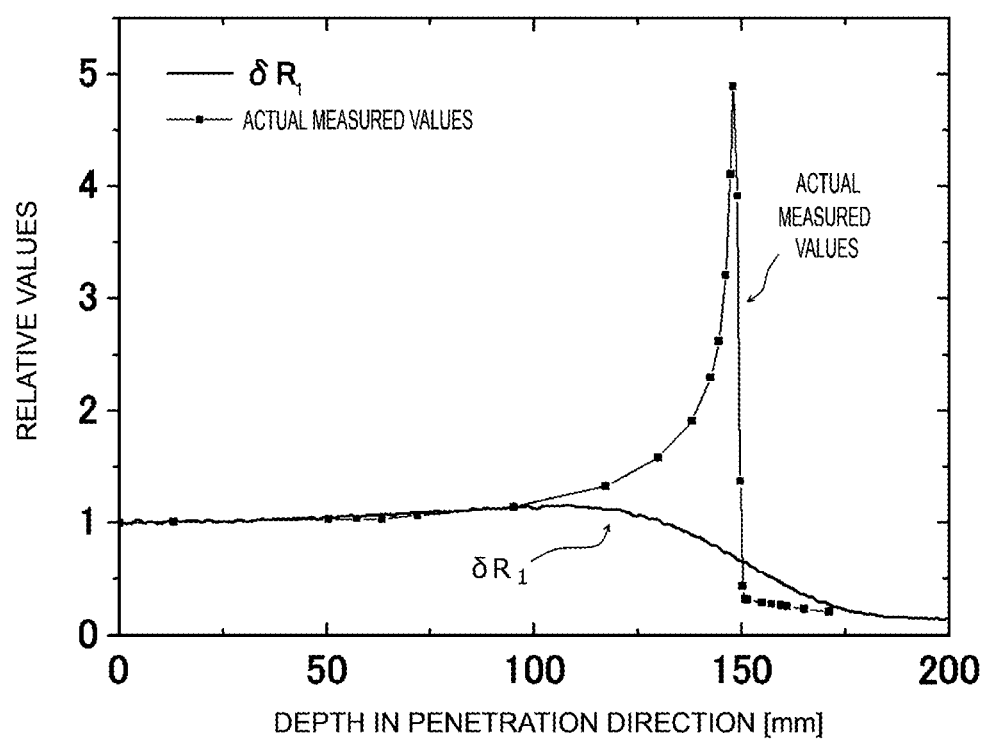
FIG. 3 is a graph indicating values of gradient $\delta R_1$ that reflect change amounts of density of Fe(III) measured at positions within a Fricke gel dosimeter in the case of conventional Fricke gel dosimeter to which no clay particle is added in comparison with actually measured values of macroscopic energy deposition, or dose amounts.
Figure 4:
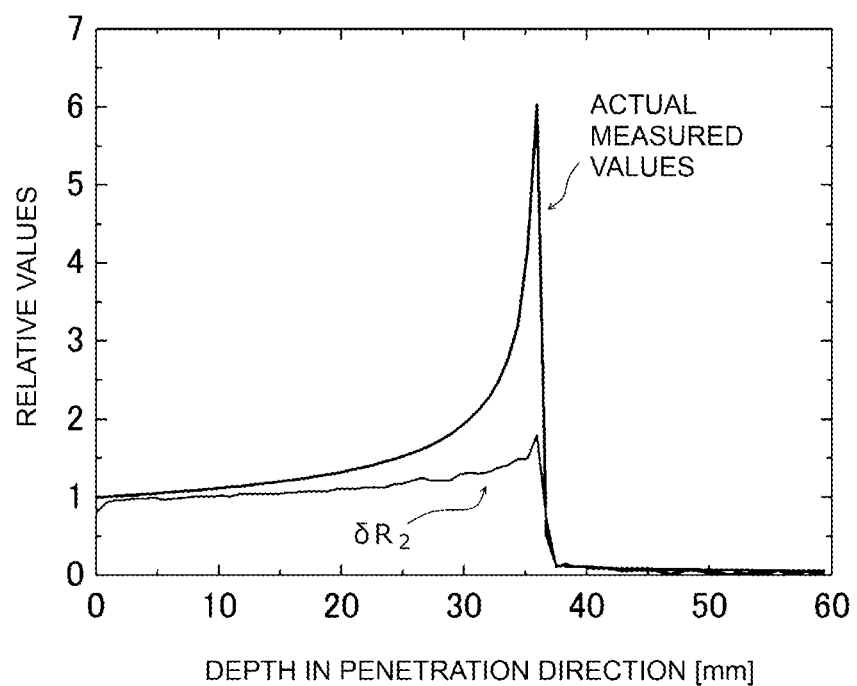
FIG. 4 is a graph indicating the values of gradient $\delta R_2$ that reflect formation density of polymers measured at positions within a polymer gel dosimeter in the case of a conventional polymer gel dosimeter in comparison with actually measured values of macroscopic energy deposition, or dose amounts.

FIG. 3 is a graph indicating the value of gradient $\delta R_1$ that reflects change amounts of density of Fe(III) measured at positions within a Fricke gel dosimeter in the case of conventional Fricke gel dosimeter to which no clay particles is added in comparison with actually measured values of macroscopic energy deposition, or dose amounts. The incident particles were carbon ($^{12}C^{6+}$) beam of 290 MeV/u. It should be noted that "MeV/u" is a unit for indicating acceleration of particles, in an expression of energy per nuclear particle. The horizontal axis denotes positions of depth in the penetration direction into the Fricke gel dosimeter, whereas the vertical axis denotes relative values of the gradients $\delta R_1$ (normalized values with a value at the incident surface) and the relative values of actually measured values by ionization chamber. The actually measured values by ionization chamber are ionization energy values measured for each transmission thickness by transmitting the carbon beams through the same material as the dosimeter having each thickness corresponding to each position within the dosimeter, and receiving the beam on the front surface of the ionization chamber. FIG. 4 is a graph indicating the values of gradient $\delta R_2$ that reflect formation density of polymers measured at positions within a polymer gel dosimeter in the case of a conventional polymer gel dosimeter, in comparison with actually measured values of macroscopic energy deposition, or dose amounts. The incident particles were carbon ($^{12}C^{6+}$) beam of 135 MeV/u. The actually measured values are similarly obtained by ionization chamber as in FIG. 3. The values of $\delta R_2$ are calculated through a similar processing with that for $\delta R_1$.

In the first place, the inventors of the present application added clay particles (nanoclay) into the conventional Fricke gel dosimeters to observe suppression effects on diffusion of the recording material by the clay particles. However, it was impossible to carry out the experiment. This was due to auto-oxidation, which will be described later. Thus, we obtained a graph of gradients $\delta R_1$ that reflects the change amounts of iron(III) ion density using a Fricke gel dosimeter without adding the clay particles. Then, as indicated in FIG. 3, the graph of the gradients $\delta R_1$ did not correspond to the graph of the actually measured values. Although the actually measured values for the dose amount had a sharp Bragg peak based on the LET's nature, the gradients $\delta R_1$ or the change amounts of iron(III) ions density only had mild change, with weaker response in comparison with the increase of the dose amount especially near the Bragg peak. We supposed this discrepancy was occurred due to two phenomena. First, weak dose response was obtained at around positions where high LET was given for the conventional Fricke gal dosimeter, or where the ionization density was high due to higher microscopic energy depositions. In addition to that, second, diffusion of the densities of the recording material took place and the densities were blurred by the diffusion under the condition that no clay particles are added. It was not clear how much these phenomena actually affected the situation. Thus we conducted another experiment, using a polymer gel dosimeter, with which no consideration was necessary for the diffusion, with different irradiation condition for different material of the dosimeter. FIG. 4 depicts this result.

As indicated in FIG. 4, the graph for the gradients $\delta R_2$ reflecting formation density of polymers in the conventional gel dosimeter had a discrepancy with the actually measured values for the dose amount. The discrepancy in FIG. 4 suggests that the conventional gel dosimeters yield smaller dose response at positions where LET values are high, or where microscopic energy deposition and high ionization densities are expected. That is, Formula (1) would not be satisfied in the conventional gel dosimeters, and therefore, linear density of the recording material with actual microscopic energy deposition at positions could not be obtained. It is to be noted that reduction of dose response at positions where ionization density is high has been reported for the conventional Fricke gel dosimeters to which no clay particles are added (See, for example, Non-Patent Document 2). In fact, according to Non-Patent Document 2, it has been observed that the value of the dose response with a proton beam, which has milder LET dependence than carbon beams, is reduced in the conventional Fricke dosimeters. The inventors of the present application believe that the values of the actual dose response around the endpoint of the range were reduced to a half or below of the value for the incident surface, based on the result in FIG. 4. It follows that, even when production amounts of iron(III) ions could be measured properly as values of R1 value with an NMR, it should be impossible for conventional Fricke gel dosimeters to accumulate microscopic energy deposition properly, and we cannot recover from the situation with conversion calculation after the measurement.

1-2. Cause of Beam Quality Dependence of Dose Response

The inventors of the present application believe the reason why the dose response in the gel dosimeter depends on the beam quality, especially on the LET, is as follows. We first have paid attention on the behavior of radicals near positions with high LETs. We suppose that ratio of the radical self-consuming reaction, in which radicals recombines with each other, may soar in high LET regions due to the high density of radicals. In most typical case, some of the radicals, once generated in proportion to the dose amount, are consumed and the ratio of the consumption would be high for high LET regions. This may be explained differently as follows: although the number of radicals (reaction radicals) that will survived up until they contribute to the production reaction of the recording material is higher for the regions with high ionization density due to the high LETs than for low ionization density regions, the number is not increased to such an extent that it keep satisfying proportionality to the number of radicals produced in proportion to the ionization density, or production radicals. At any rate, if such phenomenon is observed, then the chain of proportionality (Formula (2)) between the ionization density and the increment of recording material density is broken, and therefore, Formula (1) could not be satisfied.

To be more specific, comparing between higher and lower LET regions, it is certain in higher LET region that $e_{aq}^-$ (hydration electron), .H (hydrogen radical), and .OH (hydroxyl radical) are produced with higher density, and ratio of radicals having shorter distances each other should be high. Since these radicals react with each other, the higher the LTE becomes, the more frequent the radical self-consuming reaction takes place. The radical self-consuming reaction is explained in the context of Fricke gel dosimeter, in such a manner that it easily occurs when hydrogen radicals .H are produced in higher density. Typical reaction for this is, for example, $$.H + .H \Rightarrow H_2.$$

In this example, .H (hydrogen radicals) are used to produce hydrogen $H_2$, the number of hydrogen radicals that should contribute in formation of recording material from the recording material precursor, or iron(III) ions from iron(II) ions, will not be so increased. Even when radicals are produced in proportion to the microscopic energy deposition that reflects the LET value, if a fraction of produced radicals that do not contribute to the following reaction is high due to the radical self-consuming reactions, then the formation density of the recording material becomes insensitive to the macroscopic energy deposition for high LET regions. For example, the recording material density around the Bragg peak in the gel dosimeter should become lower than what should be obtained. We have assumed the primary cause of the LET dependence in the dose response observed in the conventional Fricke gel dosimeter in this manner.

1-3. Addition of Clay Particles into Gel Dosimeters

In the case of polymer gel dosimeters, generally speaking, the recording materials are fixed, in Fricke gel and DCG dosimeters however the recording material is diffused in time due to thermal fluctuation that is inherent to gel composition. The inventors of the present application have taken an approach of adding clay particles to Fricke and DCG dosimeters to suppress the diffusion for Fricke and DCG dosimeters (see, Non-Patent Document 1). The type of clay particles that has been actually added is synthetic hectorite (Laponite XLG (commercial name), Rockwood Additives Limited, Widnes, Cheshire UK, or Southern Clay Products, Inc. Gonzales, Tex., USA). Such clay particle may be referred to as nanoclay.

However, it is to be noted, as stated earlier, that adding the clay particles may cause specific problems. The results of our experiments indicate that it may be impossible to cause the Fricke dosimeter with clay to act as a dosimeter when too much clay particles are added. This is caused by autonomic oxidation when the addition of the clay particles is increased, or what we call "auto-oxidation", where the oxidation is caused by itself even when no radiation is irradiated. It is not necessarily clear as to what function the clay particle has on the auto-oxidation of iron(II) ions before the reaction with radicals is initiated, or before the radiation is irradiated. However, it is certain that the clay particles facilitate the oxidation. In the present application, whichever mechanism exists behind it, such an effect that facilitates the reaction for converting the recording material precursor into the recording material is always called a "reaction facilitation effect". In the conventional gel dosimeters it should be noted that we have set an upper limit of addition amount of the clay particle to prevent the auto-oxidation as a practical manner.

2. Gel Dosimeters in Embodiment 1

Now we describe our approach of an embodiment based on the above discussion regarding the conventional gel dosimeters.

2-1. Mechanisms 2-1-1. Formation of Recording Material by Molecular Radical Derivatives The inventors of the present application have paid attention on the relationship between the MRDs and the recording material, where the MRDs are such as $H_2O_2$ (hydrogen peroxide), $H_2$ (hydrogen), and $O_2$ (oxygen) that are produced through the radical self-consuming reaction. In the case of Fricke gel dosimeters as an example, it has been known that $O_2$, as one of the MRDs, contributes to the formation of iron(III) ions. The formation reaction for the ions occurs when a substance identical to the MRDs exist, regardless of whether the substance has actually produced via the radical self-consuming reaction or not. In the actual situation in the conventional Fricke dosimeters, production of iron(III) ions that is independent from the irradiation of radiation for Fricke gel dosimeters with clay particles, or auto-oxidation, originates from dissolved oxygen.

2-1-2. Elimination of Substance Identical to Molecular Radical Derivative Before Irradiation The inventors of the present application have further noted the fact that the auto-oxidation were caused by dissolved oxygen when the clay particles are added. Moreover, we have noted also that production amount of $O_2$ as one of the MRDs from the radicals was correlated with ionization density of the radiation. Based on these, we have inferred that amount or density of the recording material (i.e., iron(III) ions) produced according to the amount or density of the produced MRDs (i.e., $O_2$) must also increase according to the increase of the dose amount. In addition to that, we have come to believe that, if such a property is ensured, reactions involving the MRDs could be included in the reactions that may be used for producing the recording material. In order for assuring the property mentioned above, it must be useful, among other things, that the gel dosimeter just before the irradiation does not contain any substance identical to the MRD at all. This is because, with such a situation, the substance identical to the MRD is limited to ones that have actually produced by the radiation.

Oxygen, for example, may be dissolved into the gel dosimeter just before the irradiation unless any specific treatment is applied, because oxygen is easily dissolved into water. Moreover, Fricke dosimeter in the form of water solution and used for quantity-determination for radiation as a chemical dosimeter, is sometimes used while air or oxygen is dissolved to a saturation condition to have maximized dissolved oxygen concentration. In contrast to that, however, removing $O_2$ intentionally from the gel dosimeter must be effective in practicing the above-mentioned concept. This is because such a removal makes it possible to limit $O_2$ that may contribute to generation of the recording material to $O_2$ as the MRD that was actually produced from radicals.

2-1-3. Expectation on Mechanisms for Reduction of Beam Quality Dependence in Dose Response In the above mentioned case, we have estimated that the relationship between the microscopic energy deposition and the increment of the recording material as in Formula (1) is maintained through the following relationship:

$$\text{Ionization density} \propto (\text{radical density} + \text{MRDs density}) \propto \text{increment of the recording material density} \quad \text{Formula (4)}.$$

As indicated in formula (2), what has been paid attention are only reactions according to the water-originating radicals; that is, reactions according to MRDs have never been taken into account. In contrast to this, if our expectation mentioned above is proper, even when shortage in water-originating radicals occurs due to the radical self-consuming reactions, such a shortage in density of the radicals can be compensated by the MRDs. That is, after the reactions with respect to the MRDs are included, and if the proportional relationship is maintained between the increment of the recording material density and a quantity of (radical density+MRD density), then, even when quantitative balance between the radical density and the MRDs density changes according to the beam quality such as the LET, such change of balance would not affect the dose response of the recording material density. That is, if our expectation mentioned above is proper and the relationship in Formula (4) holds, then the increment of the recording material density is made proportional to the radicals produced according to the ionization density, thereby beam quality independent (LET independent) gel dosimeters could be manufactured.

In the present embodiment, the circumstance is made suitable for the recording material to be produced according to the microscopic energy deposition, by maintaining the relationship in Formula (4). For such a purpose, a process to remove a substance identical to the molecular radical derivative is carried out before irradiation of the radiation. If the substance identical to the MRD is contained in the dosimeter before the irradiation of the radiation, not only the density of the MRD due to the irradiation, but also the density of the substance before the irradiation comes into the production of the recording material as in MRD in Formula (4). Such a situation can be avoided if the substance identical to the MRD is excluded before irradiation of the radiation.

2-1-4. Compatibility with Function of Clay Particles

As stated earlier, the clay particle has not only a function to suppress diffusion ("diffusion suppression effect"), but also a function for facilitating reaction (See, Section 1-3). The details of this function are unclear so far. For the conventional gel dosimeters, the function is related to auto-oxidation and is not always preferable. In contrast, the function for facilitating reaction can be concluded as preferable in Embodiment 1. First of all, no auto-oxidation occurs in the present embodiment, in which oxygen for the substance identical to the MRD is removed in advance. Thus there is no chance that the function for facilitating reaction regarding oxidation before irradiation causes such a problem. Moreover, the function for facilitating reaction in the clay particles is rather considered favorable in Embodiment 1 where the MRDs are used for formation of the recording material. This is because it ensures production of iron(III) ions by an MRD, or $O_2$. If the MRD generated via radicals by the radiation contributes to formation of the recording material with certainty, then a relationship:

$$(\text{radical density} + \text{MRD}) \propto \text{increment of recording material density}$$

is held, thereby the MRDs, for example, contribute the increment of the recording material with certainty.

The inventors consider that one of causes for the function for facilitating reaction may be explained without contradiction with our expectation in Section 2-1-3. In short, we suppose the function for facilitating the reaction is related to catalysis action in the clay particles. When decomposition of $H_2O_2$, which is one of the MRDs, is facilitated by the catalysis action of the clay particles, $O_2$ will be produced. Here, $O_2$, which is also an MRD, increases sensitivity through oxidation (oxygen sensitizing effect). It is probable that a possible shift (desensitization) caused by high LET value regarding relationship between ionization density and increment in the recording material density in Formula 2, could be compensated, or cancelled, by the $O_2$ because of this catalysis action. We suppose this would be the origin of the independence of the dose response from the LET. Therefore, we consider that the oxygen sensitizing effect is a typical mechanism of the function for facilitating reaction, and that the oxygen sensitizing effect is brought about by the catalysis action of the clay particles. It should be noted however that the function for facilitating reaction is always effective in Embodiment 1 regardless of what mechanisms supports the function.

2-2. Specific Structure of Gel Dosimeters in Embodiment 1

Now specific structure of gel dosimeters in Embodiment 1 will be described, as an entity embodying the concept and expectation mentioned above.

A gel dosimeter for dose measurement of radiation in Embodiment 1 contains water, gelling agent, clay particles and recording material precursor, as conventional gel dosimeter with clay particles. As for ingredients in common with the conventional gel dosimeter with clay particles, water acts as solvent or disperse medium and is a primary component that is ionized by the radiation. The gelling agent is added into solution or mixed liquid (dispersion) having at least some degree of fluidity, such as solution, slurry (in the case clay particles are included), or sol, to form a gel while keeping their solution or dispersion state. The clay particles are added for the diffusion suppression effect, which is one of the purposes to add the clay particles. The recording material precursor contains an atom or ion that forms recording material in the manufactured dosimeter.

When the atom or ion contained in the recording material precursor changes a valence number, it will form the recording material. If we explain this in connection with the Fricke gel dosimeter as an example, the atom or ion is iron(II) ion, or $Fe^{2+}$, and the recording material is iron(III), or $Fe^{3+}$. The recording material precursor in this example is any material that may generate $Fe^{2+}$ in a certain amount. Thus, the recording material precursor has an atom or ion whose valence number is to be changed. The atom or ion will react with any of radicals that are generated by ionization, and will form the recording material.

In the gel dosimeters in Embodiment 1, above-mentioned atom or ion contained in the recording material precursor reacts not only with the water-originating radicals, but with the MRDs, or molecules that have been produced from reacted water-originating radicals with each other, and yields recording material of the same type as one to be produced via the radicals. Therefore, the reaction for forming the recording material in the gel dosimeter in Embodiment 1 is related to both the water-originating radicals and the MRDs.

A gel dosimeter in Embodiment 1 is manufactured to be free from a substance identical to the MRD before the radiation rays are irradiated. The "substance identical to the MRD" in this context is a material that would exist with arbitrary causes while it is of the same kind as the MRD in terms of the material. Materials fall within the scope of the material identical to the MRD may include an added material on purpose and a material that exists without being paid any attention as well. By way of example of the Fricke gel dosimeters, oxygen, which has been dissolved in the water contained in the Fricke gel dosimeter before the irradiation of radiation, is a typical "substance identical to the MRD". This is because oxygen produced from water-originating radicals due to the irradiation of radiation in the Fricke gel dosimeter may become MRD.

In the manufacturing method in Embodiment 1, a step of removing the MRD is practiced. The step for removing the MRD is a process step for preventing a substance identical to the MRD from existing by the time the gel dosimeter is formed, that is, any process step of removing the substance from the dosimeter of any kind with any means. The specific example for the step of removing the MRD will be described later in Section 2-2-1-1-5.

The specific structure of the gel dosimeters that seem to be promising in our view will be described together with its manufacturing step.

2-2-1. Structure 1: Fricke Gel Dosimeter

What the inventors consider promising for Embodiment 1 is a Fricke gel dosimeter manufactured by adding clay particles into the ingredients for Fricke solution dosimeter, which is known to be a solution chemical dosimeter, to form a gel.

2-2-1-1. Materials and Methods

Typical material and method for the Fricke gel dosimeter with clay particles are: adding nanoclay, which is an example of clay particles, into the ingredients for Fricke solution dosimeter, which is a solution chemical dosimeters; then adding gelling agent thereto to form a gel. In the present embodiment, a process step for removing dissolved oxygen (step of removing MRD) is performed at an appropriate timing. These will be specifically described below.

2-2-1-1-1. Water and Dissolved Oxygen

Water acts as a solvent or dispersion medium for other ingredients, and at the same time, acts as a material to produce radicals through ionization by the radiation. It is possible to adopt water that has been purified as much as possible, in the present embodiment. Typical water may include any sorts of water as pure as possible as necessity, including: extra-pure water, such as RO (reverse osmosis) water and ion exchanged water, distilled water. Generally speaking, oxygen may be dissolved to a certain amount even in such extra-pure water; however the dissolved oxygen could be removed or decreased through the step of removing MRD in the present embodiment.

2-2-1-1-2. Recording Material Precursor

The recording material precursor is a substance including molecule or ion that will eventually become recording materials through variations with changing its valence number. The typical example of the precursor for Fricke gel dosimeters, including the cases of Embodiment 1, is ammonium iron(II) and ferrous sulfate(II), which will generate an iron ion(II) ($Fe^{2+}$) when the precursor is dissolved. When the water originating radicals are produced through irradiation by radiation and MRDs are produced from such radicals, the valence number is changed to form the recording material. In the case of Fricke gel dosimeter, including the cases of Embodiment 1, iron(III) ion (Fe3+) is produced as the recording material. Meanwhile, the MRDs mentioned above is oxygen, iron(III) ion (Fe3+) as the recording material is generated, the reaction that changes the valence number should be oxidation. The mechanism for producing recording materials from the recording material precursor in the specific structure of the Embodiment 1 is identical to an action for the Fricke solution dosimeter. The Fricke gel dosimeters in the specific structure in Embodiment 1 are considered to have a structure suitable for practical use since it has identical or more sensitivity to Fricke solution dosimeters.

When the Fricke gel dosimeter is manufactured in Embodiment 1, ammonium iron(II) hexahydrate (($NH_4$) $2Fe(SO_4)_2.6H_2O$) is adopted. It may be preferable to include additives that assist reaction for producing the recording medium, such as acidity regulator as necessity. For example, perchloric acid ($HClO_4$) is added for the acidity regulator in the present embodiment. Typical concentrations for the ammonium iron (II) hexahydrate and the perchloric acid are 1 mM and 50 mM for the final gel dosimeter, respectively.

An example for the recording material in addition to ammonium iron(II) in Embodiment 1 is iron(II) sulfate, where the acidity regulator for such an example is sulfuric acid, and common salt is added as necessity.

Furthermore, additional agents may be added for improving sensitivity and record preservation capability. For example, it is useful to add Xylenol Orange to suppress diffusion of iron(III) ion, which is a recording material to be formed.

2-2-1-1-3. Clay Particles

Clay particles are added into the gel dosimeters in Embodiment 1 for two reasons: for their diffusion suppression capability to prevent or suppress diffusion of the recording material, and for their function for facilitating reaction regarding oxidation. The typical substance usable as the clay particles is one with a dimension of nanometer (i.e., greater than or equal to 1 nm and less than 1 μm) particle size for each particle, and ones with average particle size is of such nanometer order. Clay particles with such particle sizes are often referred to as "nanoclay". However, the size of particles in the present embodiment is not limited specifically. Clay particles may include such material as minerals naturally produced, minerals chemically or physically processed for controlling their properties, or artificial minerals that may be synthesized through chemical processing. It is preferable to adopt such clay particles that has high purity and is capable of being dispersed easily to water in Embodiment 1 including gel dosimeters other than Fricke gel. Particularly preferable clay particles may include: water swelling hectorite, water swelling smectite, water swelling montmorillonite, water swelling saponite, and water swelling synthetic mica. These preferable clay particles have a nature of water swelling property, or water-absorbing property and expanding property in wet condition, and they result in delamination after absorbing water. These properties make these clay particles useful in preventing diffusion of the recording material mentioned above. The function for facilitating reaction with respect to the formation reaction of the recording material has distinct effects on oxidation reaction especially for Fricke gel dosimeters, and the effect can also be expected to the clay particles mentioned above. It should be noted that for clay particles adopted in the present embodiment, including the preferable clay particles mentioned above, similarly types can be combined at the time. Furthermore, when plural types of clay particles are adopted in combination, the functions for diffusion suppression and for facilitating reaction can be assigned to respective types of clay particles. Such an approach is useful for adjusting the balance between the functions for diffusion suppression and for facilitating reaction.

Typical clay particles in Embodiment 1 may be Laponite XLG (Lockwood Additives. LTD.) that is a synthetic clay falls within a water swelling hectorite, and its typical content is 1 wt % for final gel dosimeter.

It can be expected also a function for facilitating reaction with regard to oxidation mentioned above for clay particles adopted for the Fricke gel dosimeters in a specific structure in Embodiment 1. Therefore the Fricke is used for the specific structure in Embodiment 1, and resulting dosimeter may have higher sensitivity than Fricke solution dosimeter. When it comes to more general dosimeters than the Fricke gel dosimeter, the function for facilitating reaction when forming recording material between the MDR and the recording material precursor (function for facilitating reaction), should be preferable, regardless of whether the reaction is oxidation or other reaction, such as reduction.

2-2-1-1-4. Gelling Agent

Gelling agent in Embodiment 1 is any type of gelling agent that is to be added to give shape retention nature of some extent or solidity to a mixture, which should have been solution or slurry without the gelling agent. A typical gelling agent is gelatin. Other than this, any type of agent that may be used for gelling agent for gel dosimeter can be adopted in the present embodiment, such as agarose. The agarose may be added by, for example, 3 wt % for the final gel dosimeter in the case of specific structure in Embodiment 1. In addition to that, any type of gelling agent can be adopted for Embodiment 1 so long as it develops shape retention nature to a certain level under wet condition. There is no limitation on gelling operation with the gelling agent. In the case when the gelatin is used, gelling operation has step of heating while mixing a mixture prepared as solution or slurry including other ingredients than the gelling agent, and a certain amount of weighed gelatin is dissolved into the mixture. Then the mixture dissolving the gelatin is transferred to a container, which will be also used later, and is cooled in, such as a thermostat chamber or a refrigerator. In so doing, there is a change of characteristics deviation caused by the addition of oxygen or the like, however, such can be avoided by hermetical sealing, for example. Similar operation may be adopted also for agarose. These operations unique to the gelling operation need, in general, a certain burdensome task of heating while mixing, and a certain period of time for cooling. The gelling agent may be selected from organic ones generally.

2-2-1-1-5. Process of Removing MRD

Next, the process of removing MRD is described. The process is to make the gel dosimeter free from any substance identical to the MRD. Assuming that the substance identical to the MRD exists in the gel dosimeter before it is irradiated with the radiation, the process may be explained as any the process concerning any chemical or physical operation that is capable of removing or decreasing the substance, or of maintaining the substance's removed or decreased condition. Typical process for such purpose is as follows:

removal by stimulating operation or physical operation, including: heating, cooling, irradiating energy rays such as radiation or electromagnetic waves, exerting acceleration or gradients of acceleration, passing through adsorption column, discharge or removal by the addition of some kind of materials (including a reactive material, a substitution material, and catalyst), and electrochemical operation processes, including a chemical reaction, application of voltages and electric current or the like, removal by the fixation and substantially making independent from production of the recording material by adsorption, precipitation, or the like removal by changing properties by decomposition or the like, removal by the substitution process by adding a material intentionally which cannot coexist, thereby purging the substance identical to MRD, any combination of removing processes mentioned above.

In the case a Fricke gel dosimeter is adopted for the specific structure of Embodiment 1, any process of removing process of the MRD is performed in an arbitrary timing that does not impede manufacturing of the Fricke gel dosimeter. If there is a chance that the amount of the substance identical to the MRD increases again after the removing process of the MRD based on any reason except irradiation of radiation (called "contamination"), then such contamination is also prevented as necessity. For example, if the possible contamination is dissolution of oxygen in water, then oxygen in the other ingredients to be added is removed, as well as re-mixture of oxygen due to contacting with atmosphere is prevented. After the removing step of the MRD, the gel dosimeter is handled in an atmosphere substituted by oxygen free gas and is kept hermetically sealed in a sufficiently clean containers, especially when it is taken out to the uncontrolled atmospheric area, including when it is used.

It is preferable for the step of removing the MRD to add intentionally a substance called "a radical derivative blocking substance", where the radical derivative blocking substance has a function to prevent a substance identical to the MRD from existing. Particularly, it is useful to adopt a gas that does not contain oxygen for the radical derivative blocking substance for bubbling water with such a gas. In addition, it is useful for preventing contamination through such bubbling to have saturation of gasses other than oxygen, because it will prevent future dissolution of oxygen significantly. It should be noted that any substance except both oxygen and a material that increase oxygen, may be mixed or dissolved into water to which bubbling is performed, before or after the bubbling process. In other words, it is preferable in a viewpoint of practical easiness to sufficiently decrease oxygen concentration dissolved in the water by substitution with gas in a preferable structure in the present embodiment.

The radical derivative blocking substance mentioned above is preferably at least one gas selected from a group consisting of nitrous oxide gas, argon gas, nitrogen gas, and helium gas. Specifically, it is one of the favorable examples to perform bubbling of nitrous oxide (dinitrogen monoxide, $N_2O$) gas into water, and in this case, radical derivative blocking substance is the $N_2O$ gas. Of course, it is possible to decrease dissolved $O_2$ by means such as the bubbling in a similar way even if it is other types of gas such as inert gas is adopted. Oxygen, which is a substance identical to the MRD, is removed from the water when the bubbling of gas such as the $N_2O$ for a radical derivative blocking substance is performed. On top of that, since $N_2O$ slightly dissolves into a gel dosimeter by bubbling, future contamination by oxygen is avoided for the gel dosimeter. In should be noted that, there is no problem at all even if a radiation irradiates any type of gasses, including ones not described specifically. In addition, the oxygen atom of the $N_2O$ is not isolated, thus there no problem in this respect. The nitrous oxide $N_2O$ is called the laughing gas and is commonly used for anesthesia purposes in medical sites. In addition, the nitrous oxide $N_2O$ has another action depending on liquid acidity, which will be explained in detail in Embodiment 2.

Therefore, a process to remove oxygen by de-aeration in any stage before the gel formation is also a preferable example for the step of removing the MRD in the present embodiment. Specifically, it is preferable to adopt any of de-aeration methods: substituting de-aeration method by depressurization or pressurization, freeze substitution de-aeration method, and heating substitution de-aeration method. Moreover, it should be noted that "de-aeration" here is to express a process for decreasing or removing the substance identical to the MRE (e.g., oxygen) from ingredients with water, thus it does not matter in this regard whether there remains other type of gas (e.g., nitrogen). For example, at least the substance identical to the MRD is decreased or removed by physical operation, such as depressurization or pressurization for substituting de-aeration method by depressurization or pressurization, freezing for freeze substitution de-aeration method, and heating for heating substitution de-aeration method.

2-2-1-1-6. Relationship Between Clay Particles and Removal of MRD

The clay particles' function for facilitating reaction concerning reactions, such as oxidation, has an effect also on the substance identical to the MRD. Thus attention should be paid on the addition timing of clay particles in relation to the timing of removing the MRD. It is either timing before completing Fricke gel dosimeters when MRD should be removed, or the dissolved oxygen is removed or decreased. However, auto-oxidation may occur for clay particles having the favorable property stated above if clay particles are present before a timing to carry out removing the MRD.

Therefore, when adopting the clay particles having the property mentioned above in Embodiment 1, it is preferable that clay particles are added after the substance identical to the MRD has been removed. In other words, it is one of preferable embodiment, in that at least a part of removing the MRD is performed before the clay particles are added. When clay particles possess function for facilitating reaction about the oxidation in this specific structure, it is preferable that removing the dissolved $O_2$ first, which is step of removing the MRD, and then adding clay particles.

2-2-1-2. Typical Manufacturing method

Figure 5:
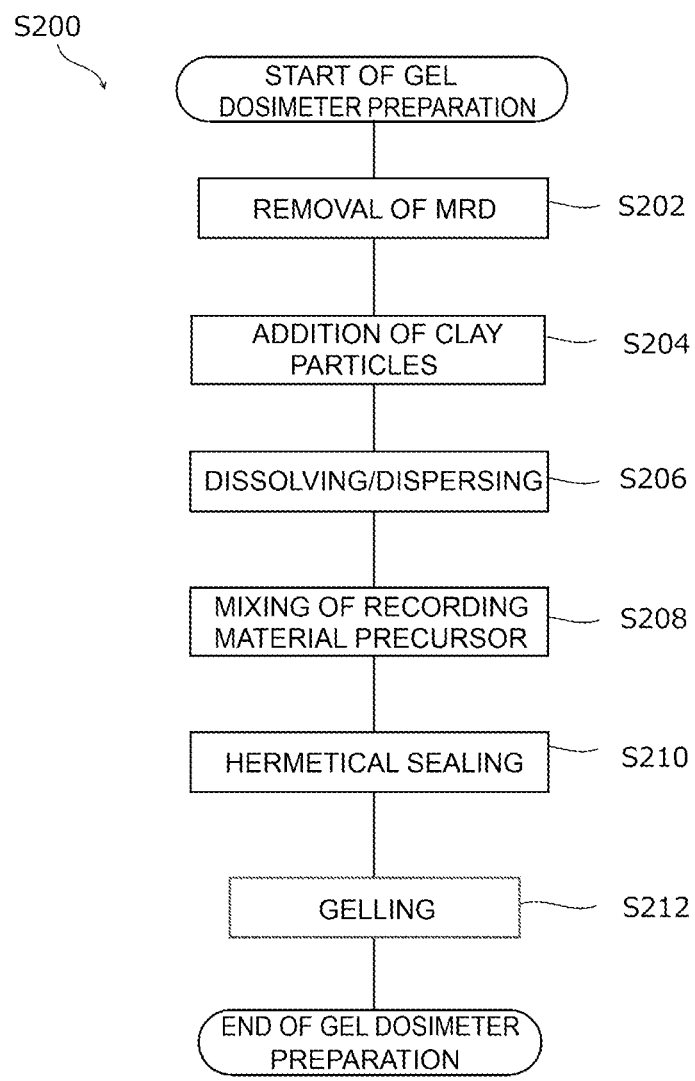
FIG. 5 is a flowchart indicating a typical manufacturing method for fabricating a gel dosimeter in Embodiment 1 of the present invention.

FIG. 5 is a flowchart indicating a typical manufacturing method for fabricating a gel dosimeter in Embodiment 1. This manufacturing method is a typical example of the detailed process of the preparation (Step S200) of the gel dosimeter which has been explained with reference to FIG. 2. The step of removing the MRD (Step S202) is such a process as bubbling extra-pure water with $N_2O$ gas. Then the clay particles are added into the extra-pure water while stirring, where the dissolved $O_2$ have been removed already (Step S204). At this moment, the gelling agent is also mixed in Embodiment 1. Then the whole parts are heated, for example, so that the mixture homogeneously is dissolved or dispersed (Step S206). Next, the recording material precursor is mixed together with additive substance (e.g., acidity regulators) as necessity (Step S208). The mixture solution prepared in this way is then hermetically sealed in a container, such as a clean glass container (Step S210). When a gelling agent is one that works by cooling, the mixture solution in the container is stored in a refrigerator or the like for a necessary period of time (Step S212). By following the above-mentioned process, a Fricke gel dosimeter of a specific structure in Embodiment 1 is manufactured. It is to be noted that there is no special difficulty in practicing this typical manufacturing method of the gel dosimeter at the site where irradiation equipment for particle treatment is installed, and thus sufficient practical utility can be expected to the method. Moreover, depending on the materials such as a gelling agent and the clay particles for gel dosimeters, or on the recording material precursor, the gel dosimeter can be manufactured by following other steps than those indicated in FIG. 5.

2-3. Working Example for Embodiment 1 (Example 1)

Next, description will be made for a working example, Example 1, of the Fricke gel dosimeter that has been described based on the specific structure for the Embodiment 1. In this working example, a Fricke gel dosimeter with nano-clay is actually manufactured, and $\delta R_1$ values measured with the Fricke gel dosimeter are compared with the dose distribution measured by an ionization chamber. In the description below of the working example, details including type of materials, use amount of materials, or ratios among them, processing details, processing orders, and specific arrangement of elements or parts, are provided; however, they may be changed as necessity, so long as the concept of the present invention is unchanged. Therefore, the scope of the present invention is not limited specifically to the description set forth below. Moreover, the drawings that have been described in the above will be also used. The same applies not only to Example 1 but also to Example 2 set forth later.

In the first place, for the step of removing MRD (FIG. 5, Step S202), dissolved oxygen was removed from extra-pure water by bubbling N2 gas for 30 minutes. Then, 3 wt % (for the final gel dosimeter) of gelatin and 1 wt % (for the final gel dosimeter) of Laponite XLG, were mixed in while agitating the extra-pure water (Step S204), to have uniform dispersion liquid by dissolving with heating (Step S206). Then 1 mM (for the final gel dosimeter) ammonium iron(II) hexahydrate, and 50 mM perchloric acid, to the final gel dosimeter, were then mixed into the dispersion liquid (Step S208). The mixed dispersion liquid was then sealed hermetically in glass container (Step S210), and a gel is formed after storing for 10 hours or more under a circumstance at 10 degree-C or below (Step S212). According to these steps, four samples of the Fricke gel dosimeter sealed in a glass container were manufactured for Example 1.

Carbon beams ($^{12}C^{6+}$) were irradiated to the samples of the Fricke gel dosimeter in Example 1 by a particle accelerator, HIMAC (Heavy Ion Medical Acceleration in Chiba) at the National Institute of Radiological Sciences (Chiba, Japan). Specifically, 100, 200, 300, and 400 Gy carbon beams having acceleration energy of 290 MeV/u were irradiated to each of the samples. The samples after irradiation were analyzed through MRI measurement by 1.5 T MRI (Intera Achieva Nova Dual, Philips). The pulse magnetic field applied for the analysis was a mixed turbo spin echo sequence, and the relaxation times T1 was obtained for incident directions to the samples, thereby $R_1$ (or $1/T_1$) values were calculated. For a reference for making a comparison, dose distribution at positions was measured by an ionization chamber in the same measurement of FIG. 4.

Figure 6:
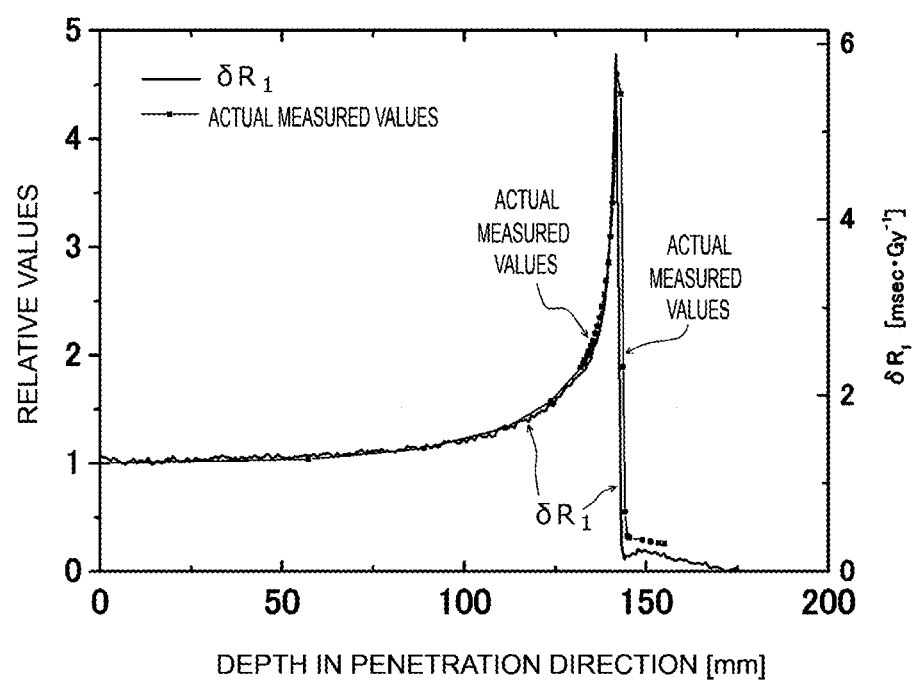
FIG. 6 is a graph indicating the values of gradient $\delta R_1$ that reflect change amounts of density of Fe(III) ion at positions within a Fricke gel dosimeter manufactured as a working example (Example 1) of Embodiment 1 of the present invention, in comparison with actually measured values of macroscopic energy deposition, or dose amounts, for corresponding positions.

The $(1/T_1)$ values or $R_1$ values obtained through MRI measurement showed distribution that reflected Bragg peaks within the samples, and, through a comparison for identical positions among samples with different dose amounts, and the values increased according to the dose amount of the radiation. FIG. 6 is a graph indicating the values of gradient $\delta R_1$ that reflect change amounts of density of Fe(III) ion at positions within a Fricke gel dosimeter manufactured as Example 1 of the present embodiment, in comparison with actually measured values of macroscopic energy deposition, or dose amounts, for corresponding positions. The horizontal axis denotes positions of depth in the penetration direction into the Fricke gel dosimeter, and the vertical axis denotes a relative value $\delta R_1$ normalized by a value at the surface of the gel dosimeter, and a relative value of the dose distribution for actually measured values by the ionization chamber, which are indicated in the left axis. The right axis gives a scale for reading $\delta R_1$ values before the normalization. As can be shown in this graph, a distribution of $\delta R_1$ values is in good agreement with the actually measured dose distribution, for the Fricke gel dosimeter of the present example. This agreement is such that any types of three dimensional dosimeters have never achieved. As is evident from the comparison with the two graphs, a graph for the distribution of $\delta R_1$ values that reflect production of iron(III) ion in the gel dosimeter of Example 1 precisely reproduced changes found in the graph of actually measured values for the macroscopic energy deposition within the material. Through Example 1 mentioned herein, we have confirmed that a Fricke gel dosimeter, a specific structure of the present embodiment, is able to measure dose amount via $\delta R_1$ values without being affected by the beam quality.

3. Embodiment 2

Another embodiment, Embodiment 2 of the present invention is described. Embodiment 2 is one for a gel dosimeter without gelling agent, which has been confirmed by the inventors of the present application for the first time. Further advantageous dosimeters are provided in Embodiment 2 for their practicability and performances, in comparison with ones in Embodiment 1. Throughout the following description of Embodiment 2, description is given mainly for differences found in the concept and structures from those in Embodiment 1, and descriptions that are not specifically set forth herein shall be the same as those for Embodiment 1. All the description regarding Embodiment 1 is incorporated herein by reference in its entirety.

3-1. Outline

The inventors of the present application conducted a series of experiments to reveal properties of gel dosimeters within Embodiment 1. In so doing, we have noted another structure of the dosimeter and another manufacturing method that do not have any practical problem, even without using gelling agent that was used for forming the gel dosimeters.

3-2. Development from Embodiment 1

Conventional gel dosimeters have used gelling agent to some extent. The dosimeters provided in Embodiment 1 have been the same in this respect. Moreover, the inventors of the present application have paid attention on the clay particles adopted in Embodiment 1 in the viewpoint of the diffusion suppression of the recording material. The auto-oxidation problem has been overcome, and the LET dependence has been removed by adopting the clay particles, as described in Embodiment 1 of the present application.

Among knowledge obtained through Embodiment 1, we have focused on the fact that the composition of a gel dosimeter, including types of materials or fraction among them, can be freely determined than ever. That is, according to the knowledge obtained through Embodiment 1, we can conclude directly that LET dependency can be removed. In addition Embodiment 1 suggests that the LET dependence can be removed in more general conditions. We can change functions and quantity of ingredients based on the knowledge regarding the reaction process. In short, we can increase the clay particles, and we can modify as to whether or not the acidity regulator should be contained, and how much it should be contained. In addition, it seemed necessary for us to have further knowledge on the function of the gelling agent.

3-3. Knowledge Confirmed through Experiments

The inventors of the present application have studied effects of the composition of the gel dosimeters by changing the composition through experiments. In particular, we measured performances by actually changing the ingredients and their amount for the purpose of analyzing the effect of the ingredients on the performances of the dosimeter. The knowledge we obtained for such results included the following. It should be noted here that the items are obtained from results under conditions similar to those of Embodiment 1 with gelling agent, unless otherwise noted.

- Based on the adjustment of addition amount of perchloric acid between 0-150 mM (relative concentration to water), no sensitivity change was found for 0-50 mM and the measurement was possible. However, there was no response for 150 mM. It should be noted that this is different from the disclosure in a scientific literature. In studies to date, Fricke gel dosimeters with higher acidity by sulfuric acid ($H_2SO_4$) have shown greater sensitivity for higher acidity, and it has lost response with no acid is added (Schulz, R. J., et al., Phys. Med. Biol., 35(12): p. 1611-1622 (1990)). This implies that acid environment is a prerequisite. In contrast, we have confirmed that acid environment is not always necessary.
- Fluidity is increased and gelling is impeded for increased perchloric acid ($HClO_4$) to have acidity environment.
- When addition amount of clay particles was increased, fluidity of solution or dispersion was reduced even when no gelling agent was added to an extent that it could be practically used as gel dosimeters. That is, the solution or dispersion including water and clay particles with fluidity, where the clay particles were contained to a certain amount, lost the fluidity and got hard when iron (III) ions were added even when no gelling agent was added, in such a manner that no practical problem was raised.
- Adding organic gelling agent, such as gelatin, made the sensitivity ($\delta R_1$ value for dose amount) small. Conversely, when such gelling agent was not used, higher sensitivity was obtained.
- $N_2O$ converted $e_{aq}^-$ (hydration electron) to .OH (hydroxyl radical) in acid and neutral conditions.
- The solution or dispersion under processing was susceptible to oxygen or the like in the atmosphere. In addition, in the case the solution or dispersion under processing was cooled or heated, the reproducibility of performance in the experiment became poor.

The pieces of knowledge we obtained includes not only ones that have been reported by the literature in the past, but also ones that cannot be explained by knowledge in the literatures, as is indicated in the items list. It should be noted that the items list above is not an exhaustive list of the pieces of knowledge we obtained through the experiments.

Unlike the conventional gel dosimeters or Embodiment 1, it is not always necessary to add gelling agent, as suggested by among other things the fact that the fluidity is lost ("solidification") even when any gelling agent such as gelatin is not used to an extent no practical problem is raised. This removes necessity of addition of gelling agent during the preparation of the gel dosimeters, alleviates manufacturing burden, and on top of that, helps to improve reproducibility in the performance. However, it is to be noted that the cause for this solidification without gelling agent is unclear at this stage. We suppose at this moment that there may be gelling action or increasing thixotropy, and thus the fluidity would be lost. That is, the clay particles are selected from various types from water swelling hectorite, water swelling smectite, water swelling montmorillonite, water swelling saponite, and water swelling synthetic mica, as preferred clay particles. These preferred clay particles have a nature of water swelling property, or water-absorbing property and expanding property in wet condition. The fluidity is significantly reduced especially when iron(II) ion is added. For example, 1 mM (for water) of ammonium iron(II) hexahydrate added to 3 wt % Laponite XLG water solution will have as high thixotropy as one in 5 wt % Laponite XLG water solution. This shows that $Fe^{2+}$ ion interacts with clay particles, and increases gelling strength. Generally speaking, when clay particles are in wet condition, $Na^+$ ions intercalated between layers of the clay are hydrated. If $Fe^{2+}$ ions come close there, $Fe^{2+}$ reacts with $Na^+$ in the layers through ion exchange reaction, and $Fe^{2+}$ gets between the layers of the clay. This changes the property of the clay particles, resulting in increase of the viscosity. This is the story based on our conjecture about mechanisms on the solidification. In our experiment, we have confirmed that clay particles in wet condition actually develop its shape retention nature (solidification). The degree of the solidification capability in this respect is such that flow of the recording materials within the container storing the dosimeter is avoided, and that the shape is maintained until the three-dimensional dose distribution is recorded and the measurement is completed. It is to be noted that gel dosimeters is practiced in Embodiment 2 regardless of which mechanism governs its solidification.

3-4. Example 2

Another working example of the gel dosimeter that can be actually practiced will be described as Example 2. The gel dosimeter manufactured in Example 2 had a sufficient solidity for practical application and satisfactory performance. Typical results will be described by a working example (Example 2) for Embodiment 2. Specific structure of Example 2 was as follows. In the first place, two types of gasses were adopted for bubbling with the radical derivative blocking substance (substitution substance) in the step of removing MRD (S202), and one piece of sample was made for each gas. Specifically, after the step of removing MRD (S202), Laponite XLG was added by an increased amount, 3 wt % (for final gel dosimeter), with agitating the extra-pure water without gelling agent added (S204). The step for dissolution and dispersing (S206) was simplified to agitation only, because heating for dissolving gelling agent was not necessary. Then 1 mM (for final gel dosimeter) of ammonium iron(II) hexahydrate was added (S208). Since neutral condition is adopted, neither acidity regulator nor perchloric acid was added. Step of gelling (S212) was substantially completed by addition of ammonium iron(II) hexahydrate (S208). In two samples for Example 2, a sample to which Ar gas was adopted in step of removing MRD (S202) is called Sample A, whereas the other sample to which $N_2O$ gas was adopted is called Sample B. For a reference of comparison, another sample was manufactured according to Embodiment 1 with 3 wt % gelatin and 1 wt % Laponite XLG, the same condition as Example 1, except that Ar is selected as a gas for the radical derivative blocking substance.

Figure 7:
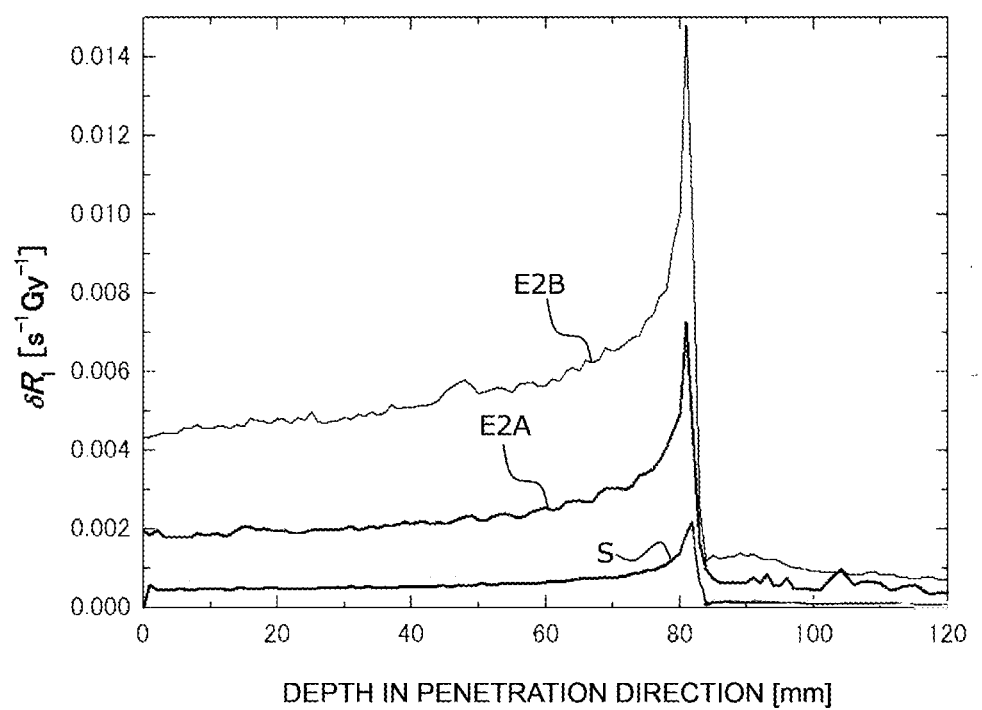
FIG. 7 is a graph indicating the values of gradient $\delta R_1$ that reflect change amounts of density of Fe(III) at positions within Fricke gel dosimeters manufactured as working examples (Example 2) of Embodiment 2 of the present invention, along with a reference sample for comparison.

Beams similar to ones in Example 1 were irradiated to the samples, with five step dose amounts of 0-600 Gy (150 Gy interval) by changing irradiation duration. Then the longitudinal relaxation rates $R_1$ (i.e., $1/T_1$) of the magnetic moment of Fe(III) ion were measured at positions of depth in the penetration direction, for the dose amounts and for the samples. Then, based on data of $R_1$ for measured five dose amount steps, the gradients $\delta R_1$ per dose amount were calculated at positions of depth in the penetration direction. FIG. 7 is a graph indicating the values of gradient $\delta R_1$ that reflect change amount of density of Fe(III) at positions within the Fricke gel dosimeter samples manufactured, for Samples A and B for Example 2 (curves E2A and E2B), and a reference sample (curve S). It should be noted that type and energy of beams irradiated were identical to ones for Example 1, therefore, their range within water equivalent substance was around 150 mm. However, LET peaks for the samples in this example were positioned at the middle along the extending direction of the containers, or color comparison tube made of glass, by inserting a PMMA range shifter (112, FIG. 1) having water equivalent thickness of 75 mm to a beam incident side. This setting was adopted because when the peak of the beam incident from the bottom of the color comparison tube is located at deep penetration depth, atmosphere near the opening of the tube may make the analysis difficult. As a result, the peaks were found around 75 mm shallower position in FIG. 7 compared to FIG. 6.

First, Samples A and B for Example 2 (curves E2A and E2B), which did not contain gelling agent, had higher sensitivity in common, than the reference sample indicated by curve S in FIG. 7. The sensitivity of Sample A of Example 2 (curve E2A), to which Ar gas was used for the radical derivative blocking substance, was more than ~2 times of one in reference sample (curve S), and its dose response was independent from LET values. Furthermore, Sample B of Example 2 (curve E2B) had higher sensitivity, ~2 times of Sample A, and around ~8-9 times of the reference sample.

Although both of the samples for Example 2 were free from gelling agent, they had no obstacles in recording the three-dimensional dose with linearity and the subsequent measurement. The samples of Example 2 was free from auto-oxidation, and had function for facilitating reaction, as explained in Section 2-1, due to the step of removing MDR (S202) carried out similarly with Example 1. Therefore, diffusion suppression of the recording material and function for facilitating reaction were realized in Embodiment 2 similarly as in Embodiment 1. In addition to that, we confirmed through actual data that 4-8 times higher sensitivity was observed in Embodiment 2. The inventors of the present application believe that it was difficult to manufacture practical dosimeters if we do not perform the step of removing MDR (S202) and a substance identical to the MDR (such as oxygen) remains. The problem of auto-oxidation would not be overcome but for this step, even if the addition amounts of clay particles were increased similarly as Example 2 in Embodiment 2.

The inventors estimate at this moment that the mechanism for the high sensitivity in samples of Example 2 would come from two factors. First factor, which relates to Samples A and B, is that they did not include gelling agent (gelatin). Second factor is that $N_2O$ not only acts as a radical derivative blocking substance, but affects oxidation reaction for recording ionization by the radiation.

The gelling agent may reduce sensitivity if it is organic material such as gelatin. Although this property has never been paid attention in conventional Fricke gel dosimeters to which no clay particle has been added, the inventors of the present application believe that such reduction in sensitivity must have worked in cases when organic gelling agent was used, including Embodiment 1. When clay particles are adopted and their nature of solidification can be expected, the need for adding gelling agent with expecting its solidification becomes weak. In particular, if the dosimeter does not contain acidic material, which may impede gelation, then the solidification performance can be obtained by relatively small amount of clay particles. This is advantageous in that sensitivity-reducing gelling agent can be removed. If high sensitivity is observed, it is advantageous, firstly, in that the radiation can be completed in shorter duration. Secondly, it is also advantageous in the case when controlling sensitivity is required for some reasons, the control may be possible in wider range because of the high sensitivity.

The fact that gelling agent is not necessary is also advantageous in practical aspect. In the case of reference sample, heating, agitating, and cooling should be precisely practiced to use the gelling functions of gelling agent such as gelatin with high reproducibility. Similar operations have to be precisely performed for another typical gelling agent, agarose. These requirements are imposed for maintaining accuracy (preciseness) in manufactured dosimeters, but are burdensome process when preparing the dosimeters. In contrast, as explained earlier in terms of preparation processes, heating and cooling processes are not necessary for dosimeter samples free from gelling agent in Example 2. The dosimeters free from gelling agent remove burdensome process operation from the preparation, and being stable, highly reproducible characteristics as well, leading to stable dose measurement. Therefore, Embodiment 2 provides us with highly practical dose measurement.

As stated above, excluding gelling agent increases sensitivity of gel dosimeters and has significant effect on practicability. However, it does not mean that gelling agent must always be excluded, even for organic ones. Embodiments adopting gelling agent for some reasons in practical aspect, are also highly practical, as indicated in Embodiment 1.

Sample B of Example 2 proved to have significantly improved sensitivity in comparison with Sample A. The inventors of the present application understand that the improvement of Sample B over Sample A originates from $N_2O$. That is, $N_2O$ has a function to convert $e_{sq}^-$ (hydration electron) to .OH (hydroxyl radical) under acidic and neutral conditions, as well as the function of a substitution material as a radical derivative blocking substance. The conversion function has some effect on oxidation when recording ionization by the radiation. Specifically, the conversion function shows different degree between the acidic and neutral conditions; in neutral condition, the effect is expressed as:

$$e_{aq}^- + N_2O \rightarrow O.^- + N_2 \quad k = 9.1 \times 10^9 \, \text{Lmol}^{-1} \, \text{sec}^{-1}$$

$$O.^- + H_2O \rightarrow .OH + OH^- \quad k = 1.7 \times 10^6 \, \text{Lmol}^{-1} \, \text{sec}^{-1} \quad \text{[Chemical Formula 1]}$$

whereas in acidic condition, the effect is expressed as:

$$e_{aq}^- + H^+ \rightarrow H. \quad k = 2.3 \times 10^{10} \, \text{Lmol}^1 \, \text{sec}^1$$

$$H^+ + N_2O \rightarrow .OH + N_2 \quad k = 2.1 \times 10^6 \, \text{Lmol}^{-1} \text{sec}^{-1} \quad \text{[Chemical Formula 2]}$$

These indicate that the conversion function from $e_{aq}^-$ (hydration electron to .OH (hydroxyl radical) exists in both conditions. However, the reaction with $e_{aq}^-$ (hydration electron) under acidic condition is a competing reaction with $H^+$ and $N_2O$, and most part reacts with $H^+$. The reaction between the products. H. (hydrogen radical) and $N_2O$, is relatively slow. Thus significant effect is observed in the case of neutral condition. Referring back to conditions in Example 1, the condition was acidic due to perchloric acid, $N_2O$ had a function only as a radical derivative blocking substance, and as a result the situation was considered to be similar to Sample A in Example 2, in which the radical derivative blocking substance was a rare gas, or Ar, though it was under neutral condition. In contrast to these. $N_2O$ used for Sample B in Example 2 should have a function to improve sensitivity through conversion function into .OH as mentioned above, as well as a function to mitigate beam quality dependence as the radical derivative blocking substance.

The embodiment of the present invention has been described specifically throughout the description set forth herein. Any parts of the description in this specification, including the embodiments and practical working examples are provided for the purpose of explaining the present invention; thus the scope of the invention should be determined based on recitations of the claims. Furthermore, any other variations based on any combination in the embodiment are included in the present invention, which variations should be also within a scope of the present invention.

INDUSTRIAL APPLICABILITY

The present invention may be utilized for establishing treatment plans of particle therapy that use particle therapy apparatus, and QA/QC for such apparatus.

REFERENCE SIGNS LIST

102 wobbler magnet
104 scatterer
106 screen with aperture
108 monitor sensor
110 ridge filter
112 range shifter
114C collimator
114MLC multi-leaf collimator
116 compensator (bolus)
118 gel dosimeter
118A record density distribution
200 MRI apparatus
202 excitation coils
204 pick-up coils

What is claimed is:

1. A gel dosimeter for measuring radiation dose comprising:
   water, as solvent or disperse medium:
   clay particles;
   recording material precursor having an atom or ion, wherein the atom or ion changes a valence number by reacting with both of a radical and a molecular radical derivative the radical being any of radicals to be generated from the water ionized by irradiation with radiation rays, and the molecular radical derivative being a molecule to be formed from the radicals that are bonded with each other; and
   a radical derivative blocking substance, wherein the radical derivative blocking substance prevents a substance identical to the molecular radical derivative from remaining, wherein the water, the clay particles, and the recording material precursor are dissolved or dispersed with each other, wherein the gel dosimeter is free from a substance identical to the molecular radical derivative before being irradiated with radiation rays, wherein the gel dosimeter ha lost fluidity by the time irradiation with radiation rays occurs, wherein the molecular radical derivative is oxygen, and wherein the radical derivative blocking substance is a gas that does not contain oxygen.

2. The gel dosimeter according to claim 1,
wherein the radical derivative blocking substance is at least one type of gas selected from a group consisting of argon gas, nitrogen gas, and helium gas.

3. The gel dosimeter according to claim 1,
wherein the radical derivative blocking substance is nitrous oxide gas.

4. The gel dosimeter according to claim 1,
wherein the atom or ion is one that is to be oxidized by reacting with both of the radical and the molecular radical derivative.

5. The gel dosimeter according to claim 4,
wherein the recording material precursor includes at least one of ammonium iron(II) and iron(II) sulfate, and
wherein the atom or ion is an iron(II) ion.

6. The gel dosimeter according to claim 1,
wherein the clay particle is such that it accelerates the reaction in which the atom or ion in the recording material precursor changes a valence number by the molecular radical derivative.

7. The gel dosimeter according to claim 1,
wherein the clay particle is at least one selected from a group consisting of water swelling synthetic hectorite, water swelling smectite, water swelling montmorillonite, water swelling saponite, and water swelling synthetic mica.

8. The gel dosimeter according to claim 5,
wherein liquid solution or dispersing liquid lost fluidity by action of iron(II) ion, which is the atom or ion, on the clay particle in wet condition, thereby the dosimeter has lost fluidity.

9. The gel dosimeter for measuring radiation dose according to claim 1, further comprising gelling agent for gelling the dosimeter.

10. A method for manufacturing a gel dosimeter for measuring radiation dose comprising:
a step of forming the gel dosimeter by dissolving or ispersing water, clay particles, and recording material precursor with each other,
wherein the water is solvent or disperse medium, and the recording material precursor has an atom or ion,
wherein the atom or ion changes a valence number by reacting with both of a radical and a molecular radical derivative, the radical being any of radicals to be generated from the water ionized by irradiation with radiation rays, and the molecular radical derivative being a molecule to be formed from the radicals that are bonded with each other,
wherein the step of forming the gel dosimeter includes a step of eliminating fluidity of the gel dosimeter by the time irradiation with radiation rays occurs,
wherein the method further comprising, at any stage before the gel dosimeter is formed, a step of removing the molecular radical derivative by excluding a substance identical to the molecular radical derivative from the gel dosimeter to be formed, and wherein the step of removing the molecular radical derivative is removing oxygen from the water, as the solvent or the dispersion medium, at any stage before fluidity of the gel dosimeter is eliminated, by any degassing method of substitution degassing with pressurization or depressurization, freeze-substitution degassing, or heat-substitution degassing.

11. The method for manufacturing the gel dosimeter according to claim 10,
wherein the clay particles have effects of swelling and gelling, or an effect of increasing viscosity, and
wherein the step of eliminating fluidity of the gel dosimeter includes either a step of gelling solution liquid or dispersion liquid having the water, the clay particles, and the recording material precursor, or a step of increasing viscosity of the solution liquid or the dispersion liquid, by use of the clay particles.

12. The method for manufacturing the gel dosimeter according to claim 10,
wherein the clay particle is at least one selected from a group consisting of water swelling synthetic hectorite, water swelling smectite, water swelling montmorillonite, water swelling saponite, and water swelling synthetic mica.

13. The method for manufacturing the gel dosimeter according to claim 10,
wherein the clay particle is such that it accelerates the reaction in which the atom or ion in the recording material precursor changes a valence number by the molecular radical derivative, and
wherein the step of removing the molecular radical derivative is performed at a stage before the clay particle is added.

14. The method for manufacturing the gel dosimeter according to claim 10,
wherein the atom or ion is one that is to be oxidized by reacting with both of the radical and the molecular radical derivative,
wherein the recording material precursor includes at least one of ammonium iron(I) and iron(II) sulfate,
wherein the atom or ion is an iron(II) ion, and
wherein the step of eliminating fluidity of the gel dosimeter is such that liquid solution or dispersion liquid loses fluidity by action of an iron(II) ion, which is the atom or ion, on the clay particle in wet condition.

15. A method for manufacturing a gel dosimeter for measuring radiation dose comprising;
a step of forming the gel dosimeter by dissolving or dispersing water, clay particles, and recording material precursor with each other,
wherein the water is solvent or disperse medium, and the recording material precursor has an atom or ion,
wherein the atom ion chances a valence number by reacting with both of a radical and a molecular radical derivative, the radical being any of radicals to be generated from the water ionized by irradiation with radiation rays, and the molecular radical derivative being a molecule to be formed from the radicals that are bonded with each other,
wherein the step of forming the gel dosimeter includes a step of eliminating fluidity of the gel dosimeter by the time irradiation with radiation rays occurs,
wherein the method further comprising, at any stage before the gel dosimeter is formed, a step of removing the molecular radical derivative by excluding a substance identical to the molecular radical derivative from the gel dosimeter to be formed, and wherein the step of eliminating fluidity of the gel dosimeter includes a step of forming a gel by adding a gelling agent into liquid solution or dispersion liquid that contains the water, the clay particle, and the recording material precursor.

16. The method for manufacturing the gel dosimeter according to claim 15, wherein the step of removing the molecular radical derivative is a step of mixing a radical derivative blocking substance as a part of composition of the gel dosimeter, the radical derivative blocking substance preventing a substance identical to the molecular radical derivative from remaining.

17. The method for manufacturing the gel dosimeter according to claim 15, wherein the clay particle is at least one selected from a group consisting of water swelling synthetic hectorite, water swelling smectite, water swelling montmorillonite, water swelling saponite, and water swelling synthetic mica.

18. The method for manufacturing the gel dosimeter according to claim 15, wherein the clay particle is such that it accelerates the reaction in which the atom or ion in the recording material precursor changes a valence number by the molecular radical derivative, and wherein the step of removing the molecular radical derivative is performed at a stage before the clay particle is added.

19. The method for manufacturing the gel dosimeter according to claim 15, wherein the atom or ion is one that is to be oxidized by reacting with both of the radical and the molecular radical derivative, wherein the recording material precursor includes at least one of ammonium iron(II) and iron(II) sulfate, wherein the atom or ion is an iron(II) ion, and wherein the step of eliminating fluidity of the gel dosimeter is such that liquid solution or dispersion liquid loses fluidity by action of an iron(II) ion, which is the atom or ion, on the clay particle in wet condition.

\* \* \* \* \*